(12) United States Patent
Yelin et al.

(10) Patent No.: US 10,994,992 B2
(45) Date of Patent: May 4, 2021

(54) METHOD AND SYSTEM FOR MANIPULATING A CELL

(75) Inventors: Dvir Yelin, Haifa (IL); Limor Minai, Kfar-Vradim (IL); Daniella Yeheskely-Hayon, Haifa (IL)

(73) Assignee: Technion Research & Development Foundation Limited, Haifa (IL)

(*) Notice: Subject to any disclaimer, the term of this patent is extended or adjusted under 35 U.S.C. 154(b) by 2562 days.

(21) Appl. No.: 13/353,467

(22) Filed: Jan. 19, 2012

(65) Prior Publication Data

US 2012/0191163 A1 Jul. 26, 2012

Related U.S. Application Data

(60) Provisional application No. 61/523,462, filed on Aug. 15, 2011, provisional application No. 61/434,448, filed on Jan. 20, 2011.

(51) Int. Cl.
| | |
|---|---|
| *A61N 5/06* | (2006.01) |
| *B82Y 5/00* | (2011.01) |
| *B82Y 40/00* | (2011.01) |
| *A61K 47/68* | (2017.01) |
| *A61K 47/69* | (2017.01) |
| *C12M 1/42* | (2006.01) |

(52) U.S. Cl.
CPC ............ *B82Y 5/00* (2013.01); *A61K 47/6849* (2017.08); *A61K 47/6923* (2017.08); *A61N 5/062* (2013.01); *B82Y 40/00* (2013.01); *C12M 35/04* (2013.01)

(58) Field of Classification Search
CPC ....................................... A61B 5/06
USPC ............ 607/88–92; 435/173.1, 173.4, 173.5, 435/449, 451; 977/904, 908, 912, 923
See application file for complete search history.

(56) References Cited

U.S. PATENT DOCUMENTS

| | | | |
|---|---|---|---|
| 6,324,257 B1 | 11/2001 | Halavee | |
| 6,530,944 B2 | 3/2003 | West et al. | |
| 6,620,154 B1 | 9/2003 | Amirkhanian et al. | |
| 7,498,565 B2 | 3/2009 | Silberberg et al. | |
| 2004/0040379 A1* | 3/2004 | O'Donnell | A61B 5/0095 73/627 |
| 2005/0203495 A1* | 9/2005 | Malak | A61B 18/203 606/9 |
| 2006/0241585 A1* | 10/2006 | Silberberg | A61B 18/20 606/45 |
| 2008/0004364 A1* | 1/2008 | Huo | B82Y 30/00 522/2 |

(Continued)

FOREIGN PATENT DOCUMENTS

| | | |
|---|---|---|
| WO | WO 01/06257 | 1/2001 |
| WO | WO 01/58458 | 8/2001 |
| WO | WO 02/28552 | 4/2002 |

OTHER PUBLICATIONS

Bahadori et al, "Hot-nanoparticle-mediated fusion of selected cells", Nano Res, vol. 10, No. 6, 2017 pp. 2034-2045.*

*Primary Examiner* — Lynsey C Eiseman

(57) ABSTRACT

A method of manipulating a living cell is disclosed. The method comprises, directing a pulsed optical field to at least one conductive nanoparticle present in the vicinity of the cell, so as to generate cavitations at or near the conductive nanoparticle at sufficient amount to effect at least one cell modification selected from the group consisting of cell-damage and cell-fusion.

34 Claims, 16 Drawing Sheets
(11 of 16 Drawing Sheet(s) Filed in Color)

(56) References Cited

U.S. PATENT DOCUMENTS

| | | | | |
|---|---|---|---|---|
| 2008/0160090 A1* | 7/2008 | Oraevsky | ........... | A61K 41/0052 |
| | | | | 424/489 |
| 2010/0189650 A1* | 7/2010 | Kim | .................. | A61K 41/0042 |
| | | | | 424/9.1 |
| 2012/0059307 A1* | 3/2012 | Harris | .................. | A61K 8/0245 |
| | | | | 604/20 |

* cited by examiner

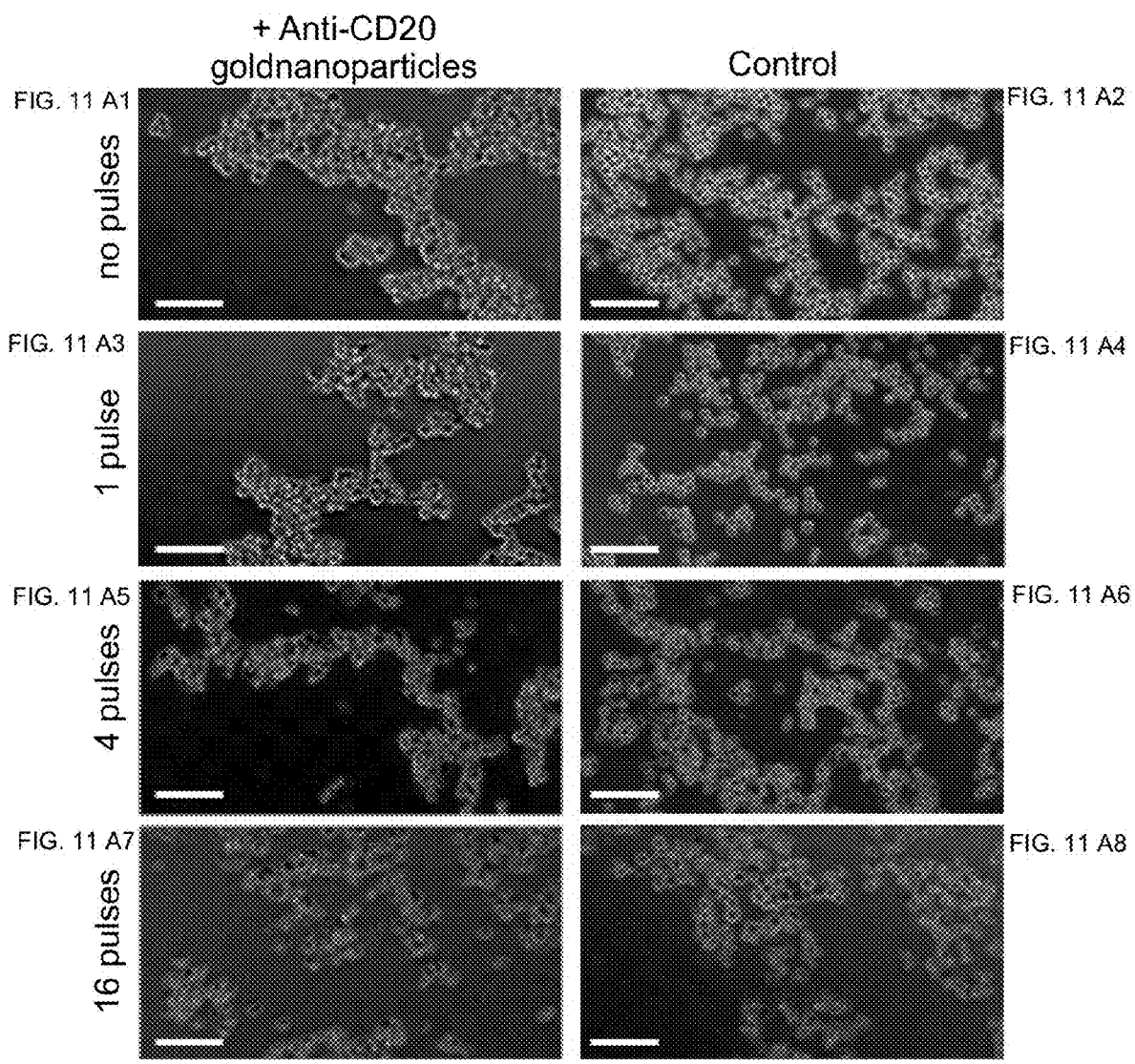
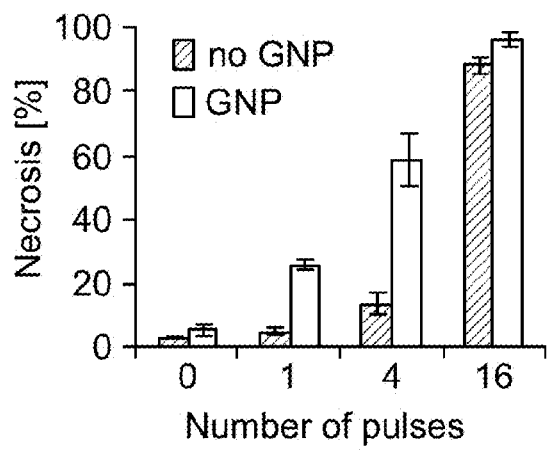
FIG. 11B
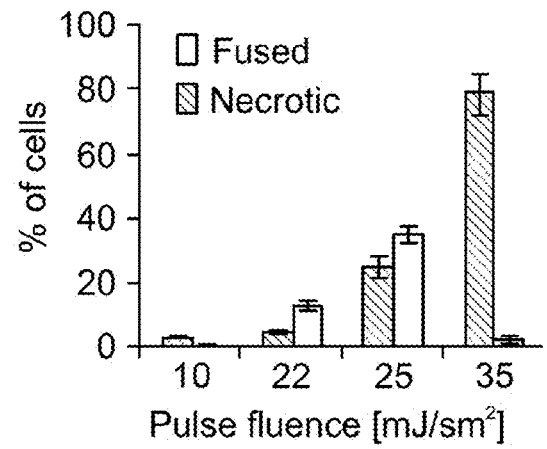
FIG. 11C

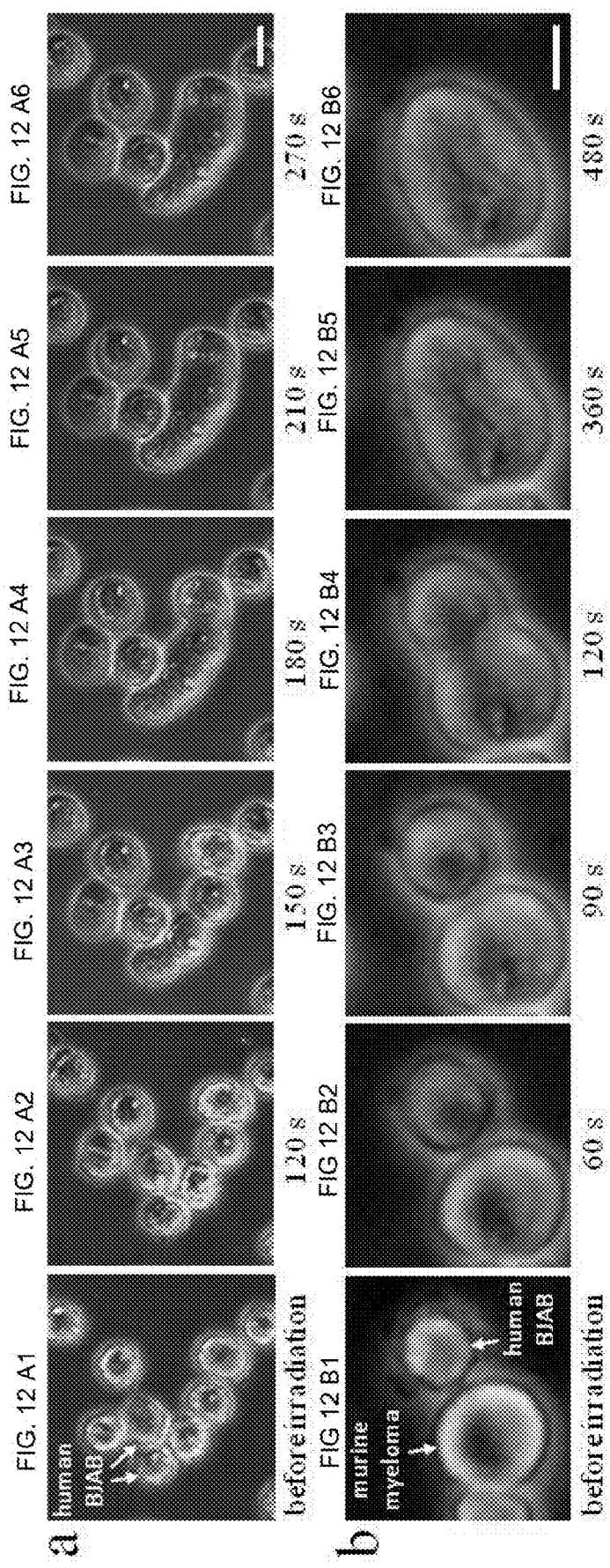

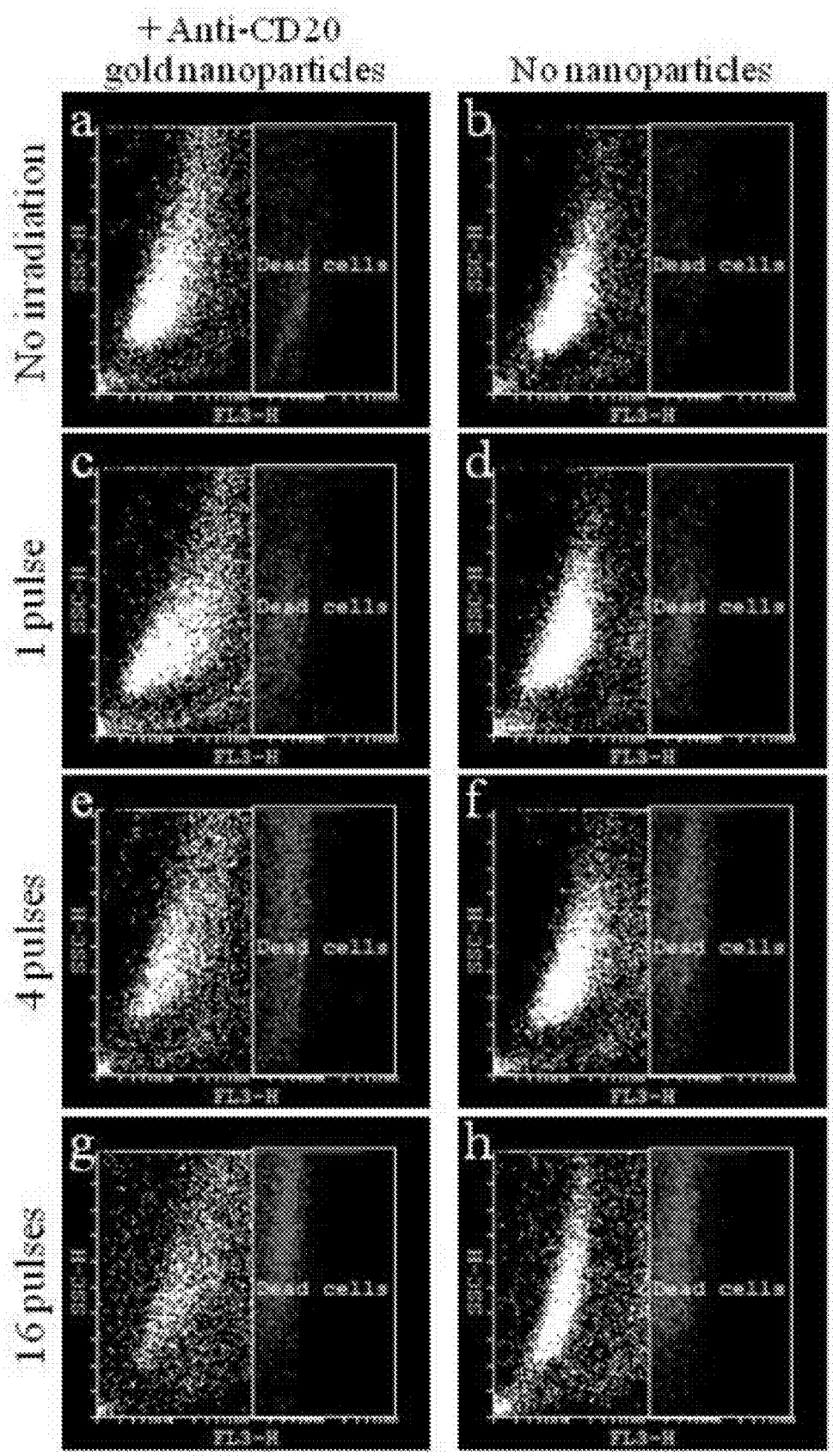
FIGs. 13A-H

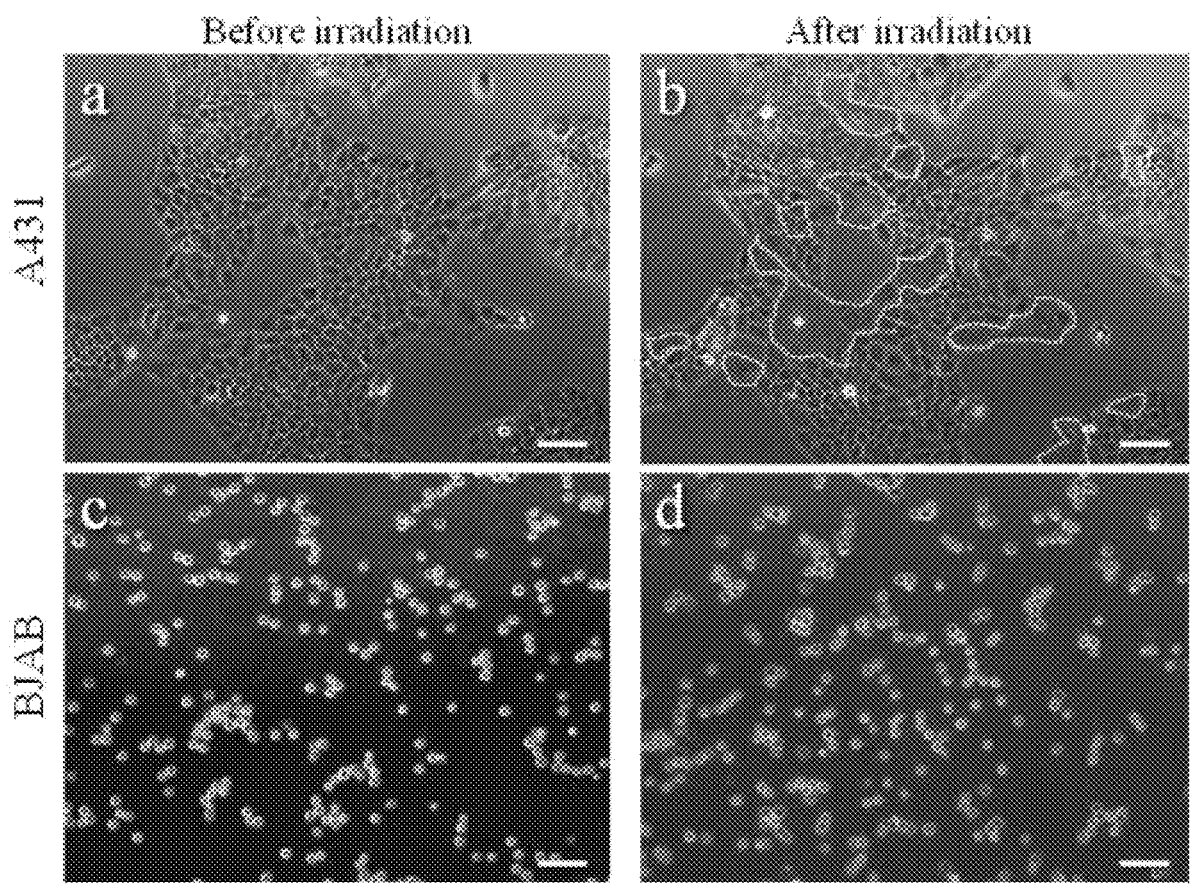
FIGs. 14A-D

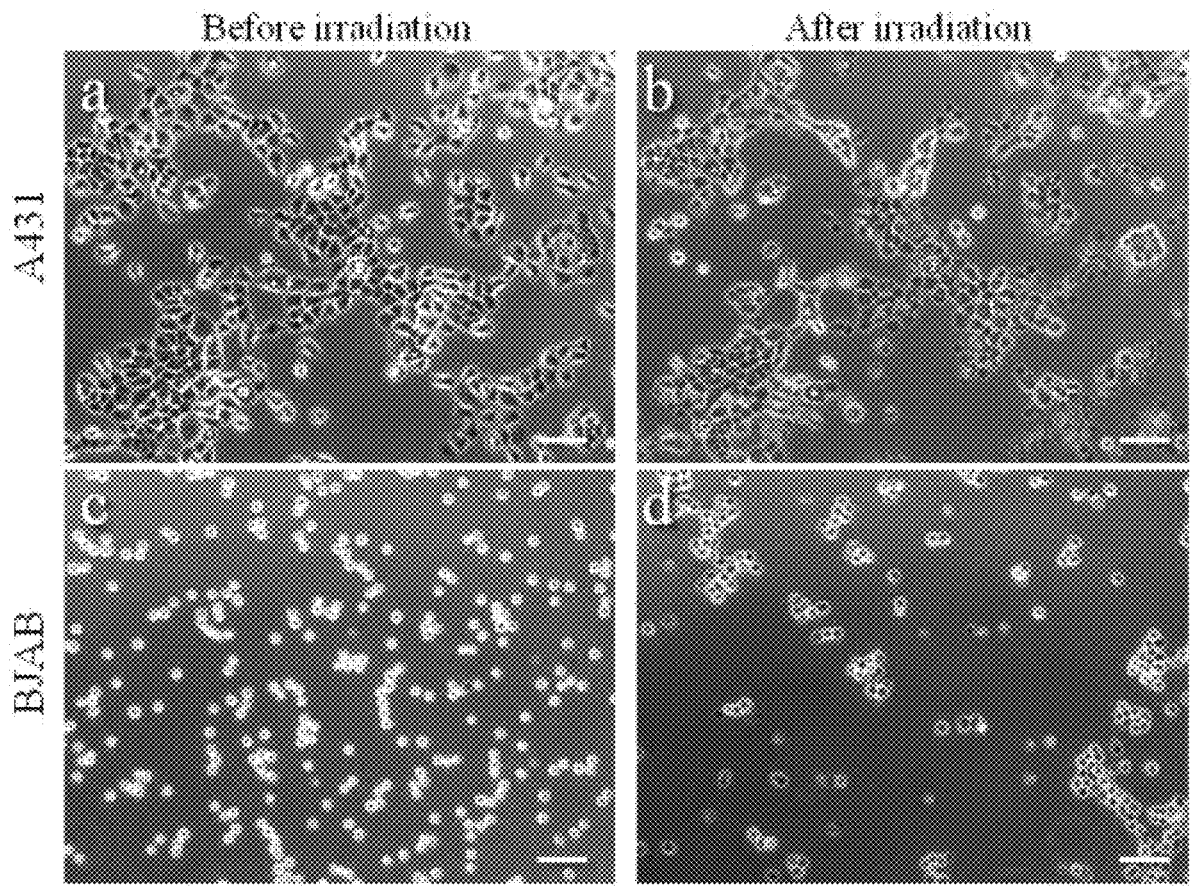
FIGs. 15A-D

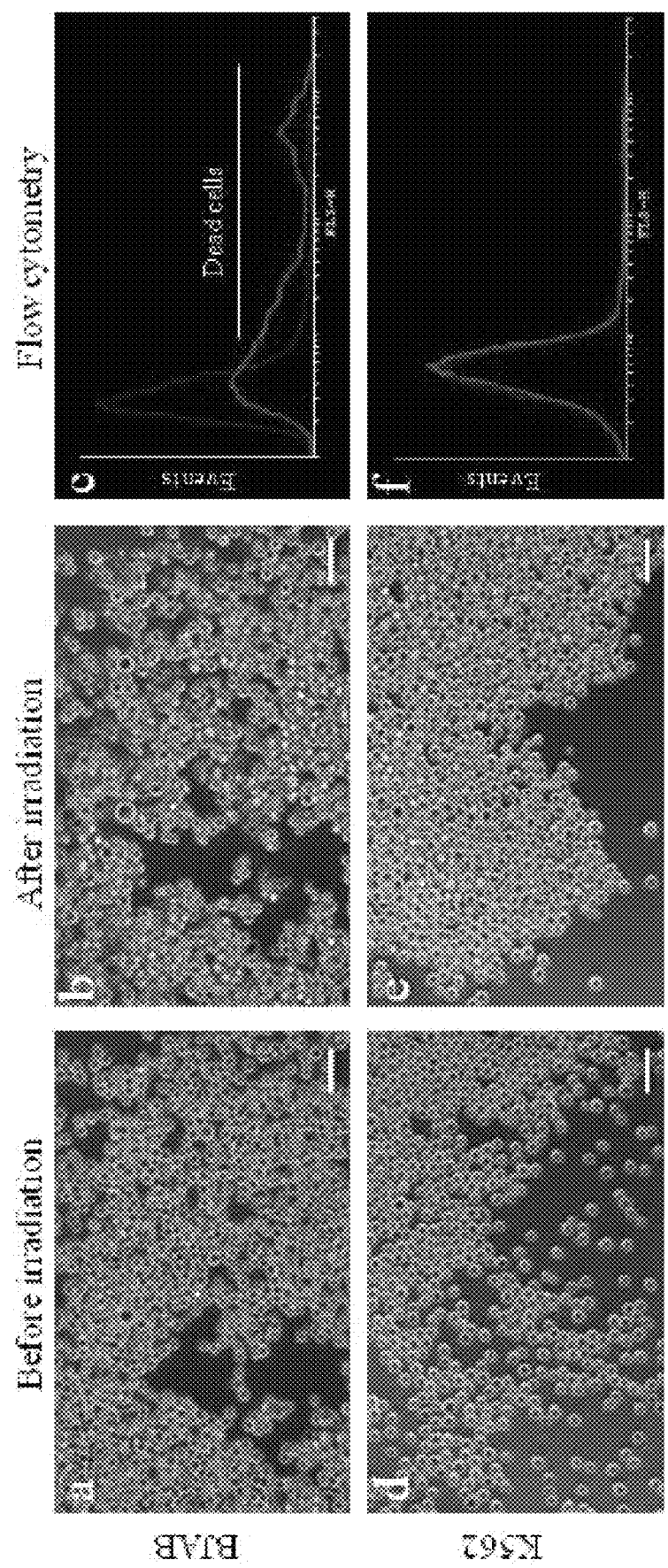
FIG. 16A-F

METHOD AND SYSTEM FOR MANIPULATING A CELL

RELATED APPLICATIONS

This application claims the benefit of priority under 35 USC 119(e) of U.S. Provisional Patent Application No. 61/434,448 filed Jan. 20, 2011, and 61/523,462 filed Aug. 15, 2011, the contents of which are incorporated herein by reference in their entirety.

FIELD AND BACKGROUND OF THE INVENTION

The present invention, in some embodiments thereof, relates to cell manipulation and, more particularly, but not exclusively, to light induced cell manipulation.

Cancer is a major cause of death in the modern world. Effective treatment of cancer is most readily accomplished following early detection of malignant tumors. Most techniques used to treat cancer (other than chemotherapy) are directed against a defined tumor site in an organ, such as brain, breast, ovary and colon tumors, etc. When a mass of abnormal cells is consolidated and is sufficiently large, either surgical removal, destruction of the tumor mass using either heating, cooling, radiative or chemical ablation becomes possible because the target is readily identifiable and localizable. However, it is not uncommon for a cancer that has initially occurred at a primary site to metastasize and spread into adjacent organs as diffuse clusters of abnormal cells. These small clusters of cells, which are more properly referred to as microscopic diffuse metastatic deposits, are not localizable and are virtually impossible to treat other than by systemic chemotherapy or radiotherapy. Yet, because of the diverse nature of cancer cells, only a portion of the metastatic abnormal cells will likely be susceptible to chemotherapy or radiotherapy, leaving abnormal cells that are resistant to the therapy to multiply until the patient dies from the concomitant effects of the malignant cells.

Recently, light and more specifically laser light has been used for non-invasive detection as well as destruction of malignant cells. Laser technology has found many applications in medicine and biology including destruction of cells or tissues, e.g., for the purpose of cancer treatment. Destruction of unwanted cells can be achieved either through a direct interaction between the laser beam and the tissue, or through activation of some photochemical reactions using light-activated molecules which are injected into or otherwise administered to the tissue.

Photo-dynamic therapy (PDT) is a relatively new approach for treating many cancers. At the first step of treatment, one or more drugs that bind to rapidly dividing cells are administered either directly to a tissue or organ or systemically to the treated subject. The drugs administered for PDT are commonly known as photosensitizers due to their inherent ability to absorb photons of light and transfer that energy to oxygen which then converts to a cytotoxic or cytostatic species. Approximately 24-48 hours after the injection, a narrow-band laser is used to excite the photosensitive drug, inducing a chemical reaction which results in a production of free radicals and/or other reactive products that destroy the abnormal tissue or cell with relatively small damage to the surrounding healthy tissue.

U.S. Pat. No. 7,498,565 discloses a method of destroying living cells. An optical pulse having an optical field power smaller than the ionization threshold of the cells is generated. Conductive nanoparticles in the vicinity of the cells locally increase the optical field power per unit area beyond the ionization threshold of the cells, and the cells are destroyed via ionization.

In the areas of disease diagnosis and the treatment of infection and diseases, monoclonal antibodies have been heretofore been suggested. The living body of a mammal possesses humoral immunity which is a defense system for specifically capturing and eliminating exogenous antigens (e.g. viruses, bacterial toxins, and chemical substances), autoantigens (e.g. autoreactive lymphocytes; cancer cells and excessive endogenous factors (e.g. cytokines, hormones, or growth factors) which are detrimental for maintaining homeostasis in the living body and can become pathogenic causing or adding to the deterioration of various diseases. In this humoral immunity, the antibodies play a major role.

An antibody has a Y-shaped basic structure comprising four polypeptide chains—two long polypeptide chains (immunoglobulin heavy chains; IgH chains) and two short polypeptide chains (immunoglobulin light chains; IgL chains). The Y-shaped structure is made when the two IgH chains bridged by disulfide bonds are connected to each of the IgL chains through another disulfide bond.

Due to this function of capturing and eliminating antigens harmful to the living body, antibodies have been utilized as drugs. Polyclonal antibodies were the earliest forms of antibody drugs, where antiserum comprising various types of antibodies against a specific antigen, were used. The method for obtaining this antiserum, however was limited to collecting from sera, and therefore, the supply was inevitably limited. Moreover, it was extremely difficult to isolate a single type of antibody molecule comprising specificity to an antigen, from this antiserum.

The successful preparation of a monoclonal antibody by Kohler and Milstein in 1975 (Nature, Vol. 256, p. 495-497, 1975) led to the solution of these problems and opened the doors for monoclonal antibodies to be used as drugs since it became possible to generate an antibody to a specific antigen on demand. Typically, the production of human monoclonal antibodies requires the immortalization of human B-lymphocytes by fusion with a partner cell-line of a myeloid source. The results of these cell fusions are named "hybridomas" and possess the qualities of both parental cell-lines: the ability to grow continually, and the ability to produce pure antibody.

Numerous cell fusion techniques have been devised over the past decades. For example, U.S. Published Application No. 20100068794 discloses a technique in which isolated cells are received and electrically fused. This publication also discloses the use of laser tweezers for applying selectivity in carrying out the cell fusion manipulation. Additional cell fusion techniques are described, e.g., in U.S. Pat. Nos. 4,806,476, 4,578,167, 4,529,694, 4,663,292, 7,402,409, 6,916,656 and 5,346,825, and in U.S. Published Application Nos. 20110045994 and 20100043882.

SUMMARY OF THE INVENTION

According to an aspect of some embodiments of the present invention there is provided a method of manipulating a living cell. The method comprises, directing a pulsed optical field to at least one conductive nanoparticle present in the vicinity of the cell, so as to generate cavitations at or near the conductive nanoparticle at sufficient amount to effect at least one cell modification selected from the group consisting of cell-damage and cell-fusion.

According to some embodiments of the invention the conductive nanoparticle is attached to the cell.

According to some embodiments of the invention the conductive nanoparticle is attached to at least two cells.

According to some embodiments of the invention the nanoparticle comprises an affinity component having affinity to the cell.

According to some embodiments of the invention the pulsed optical field is selected to generate a pressure wave in or at the cell.

According to some embodiments of the invention the pulsed optical field is selected to effect expansion of the nanoparticle by 0.1-0.5% in radius.

According to some embodiments of the invention the nanoparticle is a nanosphere.

According to some embodiments of the invention the pulsed optical field is characterized by a pulse duration in a femtoseconds time scale. According to some embodiments of the invention the pulsed optical field is characterized by a pulse duration in a picoseconds time scale.

According to some embodiments of the invention a wavelength of the pulsed optical field is from about 520 nm to about 580 nm. According to some embodiments of the invention a wavelength of the pulsed optical field is about 550 nm. According to some embodiments of the invention a wavelength of the pulsed optical field is about 532 nm.

According to some embodiments of the invention the pulsed optical field is characterized by a pulsed rate of less than 10 kHz. According to some embodiments of the invention the pulsed optical field is characterized by a pulsed rate of about 1 kHz.

According to some embodiments of the invention the directing the pulsed optical field to the nanoparticle comprises selecting the number of pulses of the optical field so as to induce apoptosis in the cell.

According to some embodiments of the invention the directing the pulsed optical field to the nanoparticle comprises selecting the number of pulses of the optical field so as to induce necrosis in the cell.

According to some embodiments of the invention the directing the pulsed optical field to the nanoparticle comprises selecting the number of pulses of the optical field so as to induce cell-fusion.

According to some embodiments of the invention the directing the pulsed optical field to the nanoparticle is done ex-vivo.

According to some embodiments of the invention the directing the pulsed optical field to the nanoparticle is done in-vivo.

According to some embodiments of the invention the cells are identical.

According to some embodiments of the invention the cells are non-identical.

According to some embodiments of the invention the cells comprise primary cells.

According to some embodiments of the invention the cells comprise immortalized cells.

According to some embodiments of the invention the non-identical cells comprise tumor cells and antibody producing cells.

According to some embodiments of the invention the non-identical cells comprise tumor cells and dendritic cells.

According to some embodiments of the invention the non-identical cells comprise stem cells and somatic cells.

According to some embodiments of the invention the stem cells are embryonic stem cells.

According to some embodiments of the invention the somatic cells are muscle cells or bone cells.

According to some embodiments of the invention the antibody producing cells are B lymphocytes. According to some embodiments of the invention the B lymphocytes are human B lymphocytes. According to some embodiments of the invention the B lymphocytes are peripheral blood mononuclear cells. According to some embodiments of the invention the B lymphocytes are murine splenic B cells.

According to some embodiments of the invention the cell is a part of a pathological tissue.

According to some embodiments of the invention the directing the pulsed optical field to the nanoparticle comprises inserting a light transmitting device into the body of a living subject having the cell therein.

According to some embodiments of the invention the inserting the light transmitting device into the body is by endoscopy.

According to some embodiments of the invention the inserting the light transmitting device into the body is by laparoscopy.

According to some embodiments of the invention the cavitations are induced by a thermal effect, and wherein the thermal effect dominates an ionization effect in the cell.

According to some embodiments of the invention the cavitations are generated while preventing cell ionization.

According to an aspect of some embodiments of the present invention there is provided a method of generating a monoclonal antibody, comprising: directing a pulsed optical field to at least one conductive nanoparticle present in the vicinity of an immortalizing cell and an antibody producing cell, so as to generate cavitations at or near the conductive nanoparticle at sufficient amount to effect fusion between the immortalizing cell and the antibody producing cell, thereby obtaining a hybridoma; and cloning the hybridoma.

According to some embodiments of the invention the method further comprising harvesting the monoclonal antibody following the cloning.

According to an aspect of some embodiments of the present invention there is provided a system for manipulating a living cell, comprising, an optical device for providing a pulsed optical field directed to at least one conductive nanoparticle present in the vicinity of a cell; and a controller configured for selecting at least one parameter of the pulsed optical field to effect at least one cell modification selected from the group consisting of cell-damage and cell-fusion.

According to some embodiments of the invention the at least one parameter is selected from the group consisting of a number of pulses, a duration of the pulses, and a repetition rate of the pulsed optical field.

According to an aspect of some embodiments of the present invention there is provided a nanoparticle. The nanoparticle being capable of specifically targeting two or more types of cells. The nanoparticle comprises a solid surface conjugated with at least two affinity components having affinity to the two or more types of cells.

According to some embodiments of the invention the solid surface is inorganic.

According to some embodiments of the invention the solid surface is conductive.

According to some embodiments of the invention the solid surface is a metal.

According to some embodiments of the invention at least one of the affinity components is an antibody, being specific to an antigen of a cell.

According to an aspect of some embodiments of the present invention there is provided a method, comprising contacting a cell population with the nanoparticle described herein such that the two or more cells of the cell population are maintained at close proximity to each other, wherein the distance between the cells is less than 5 times or less than 4 times or less than 3 times or less than 2 times the largest diameter of the nanoparticle.

According to some embodiments of the invention the method comprises directing a pulsed optical field to the nanoparticle, so as to generate cavitations at or near the conductive nanoparticle at sufficient amount to effect cell-fusion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for inducing damage in a living cell according to some embodiments of the invention;

Figure 2A:
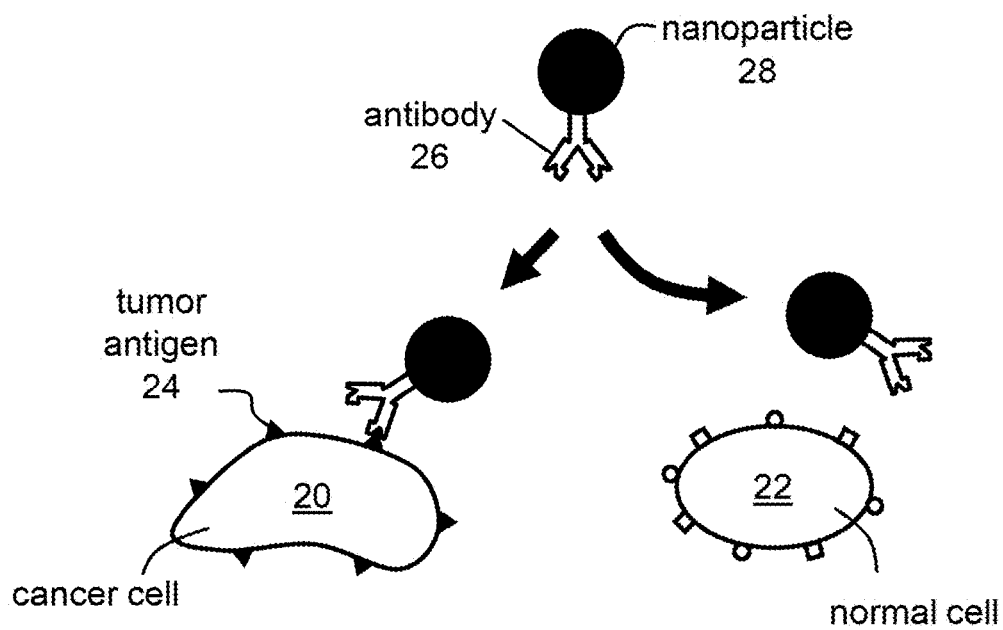
Figure 2B:
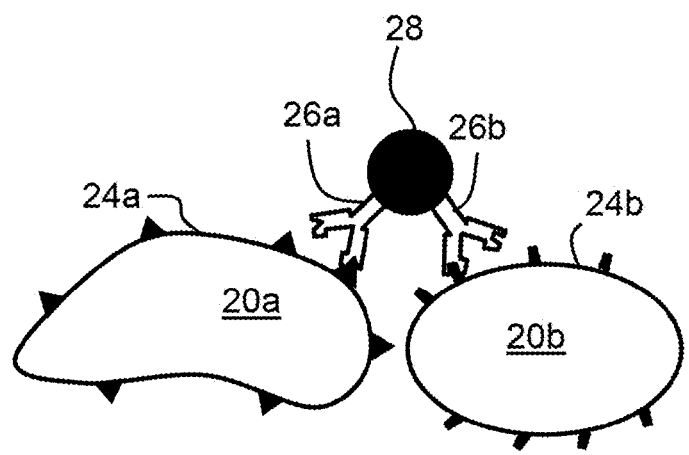
Figure 3:
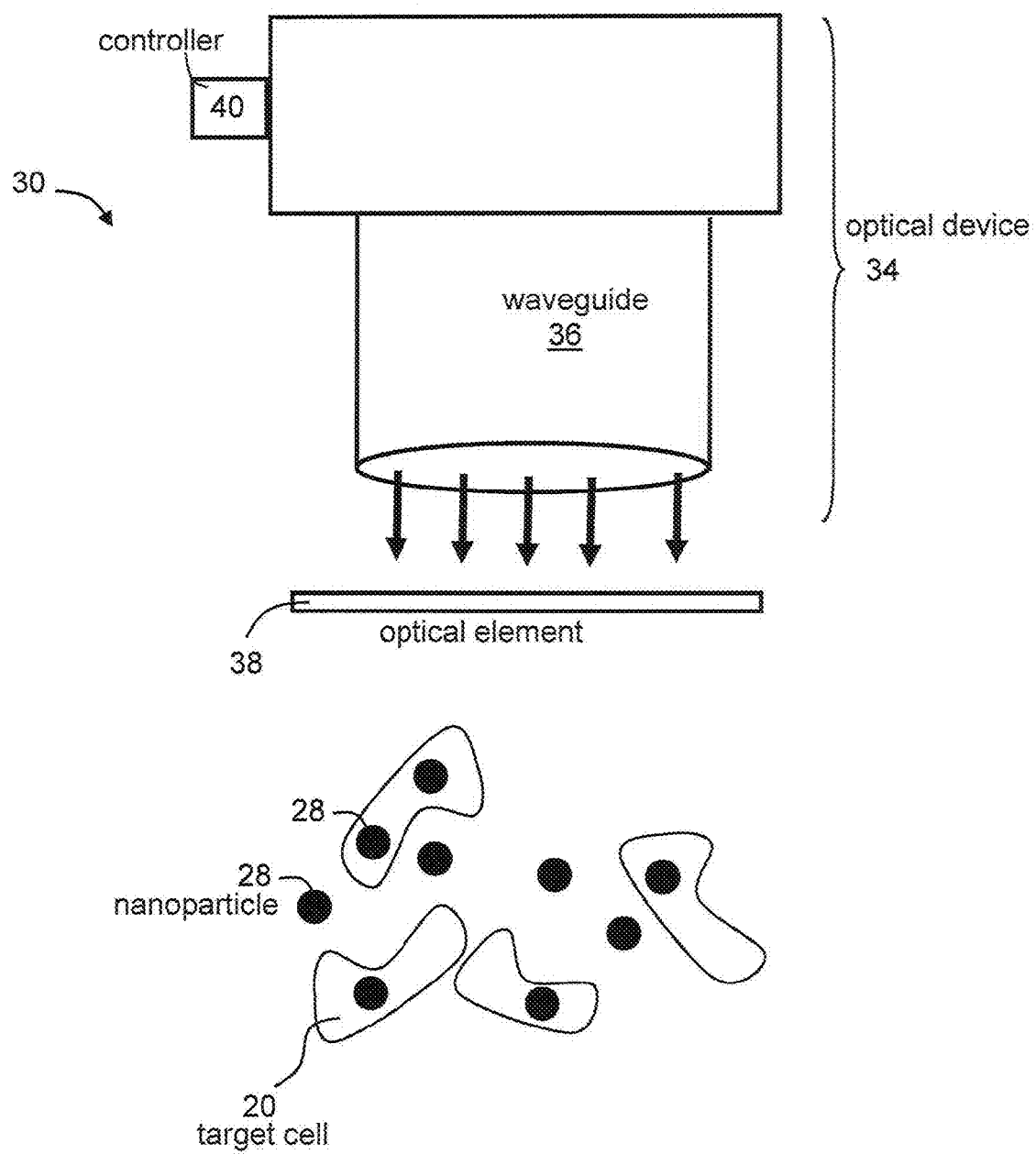
Figure 4A:
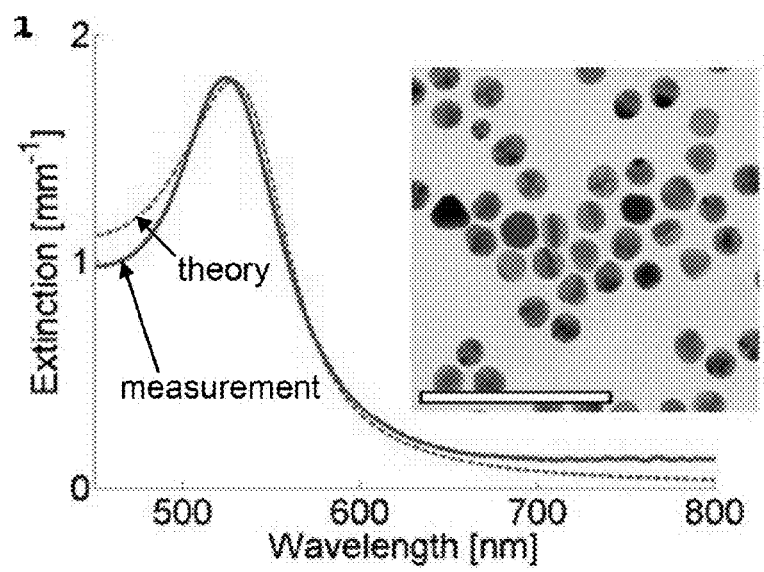
Figure 4B:
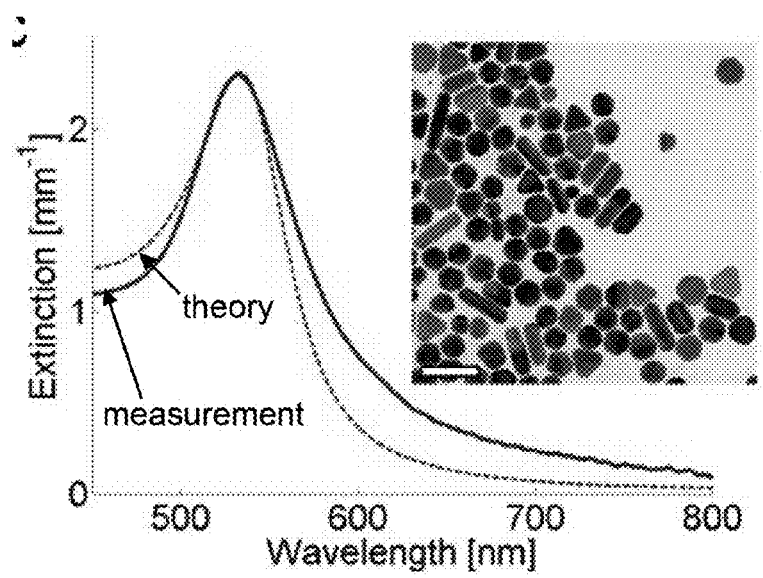
Figure 5A:
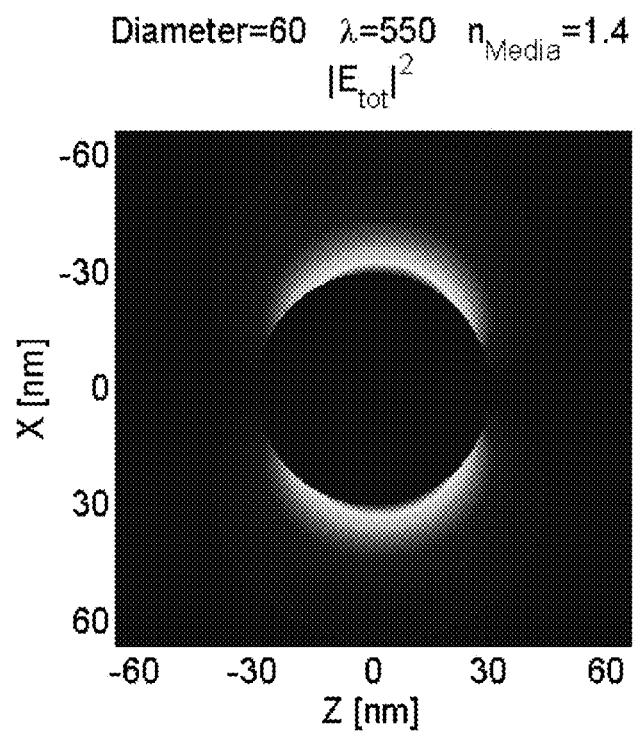
Figure 5B:
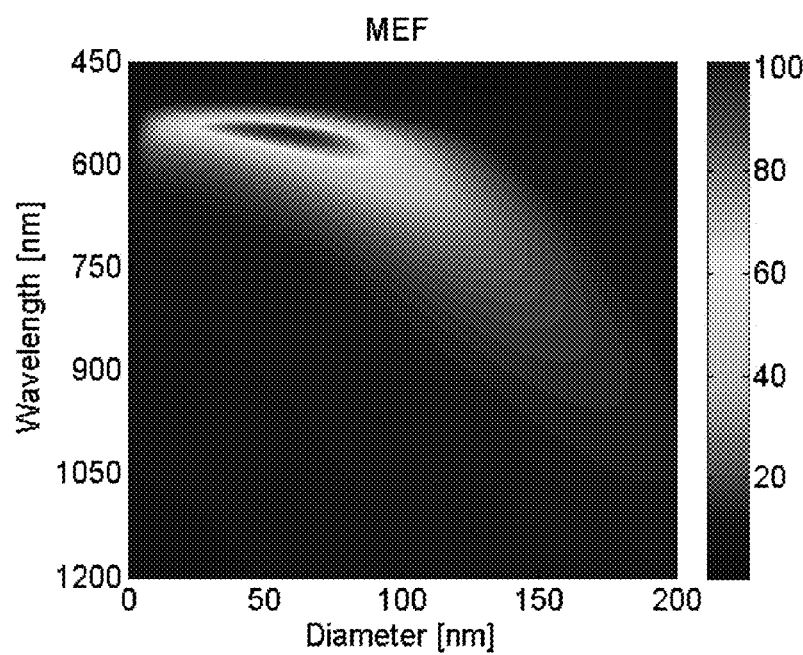
Figure 6A:
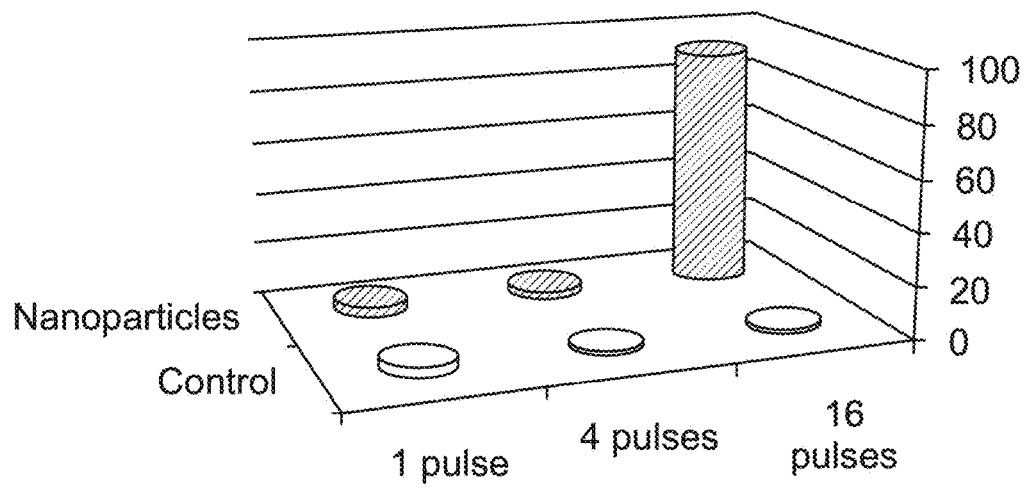
Figure 6B:
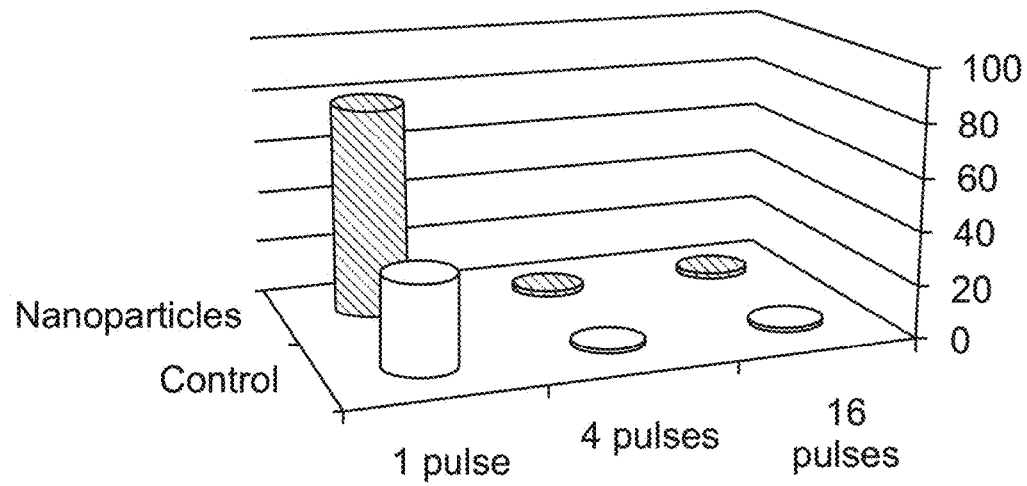
Figure 7:
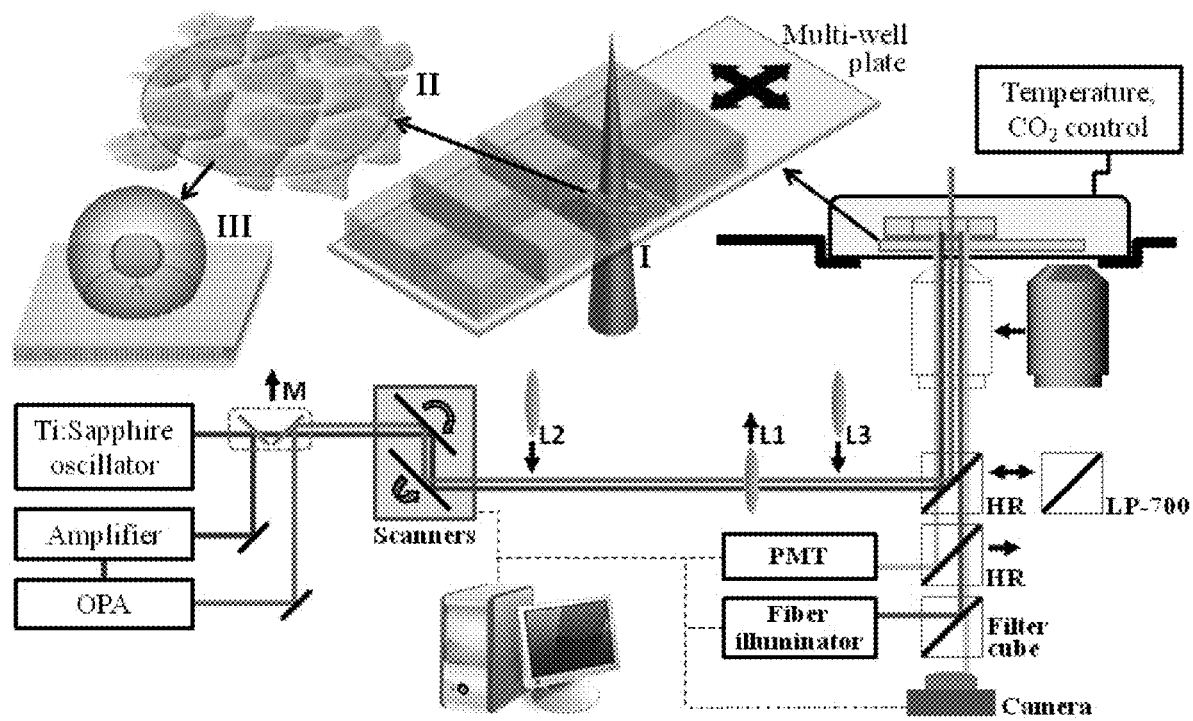
Figure 10:
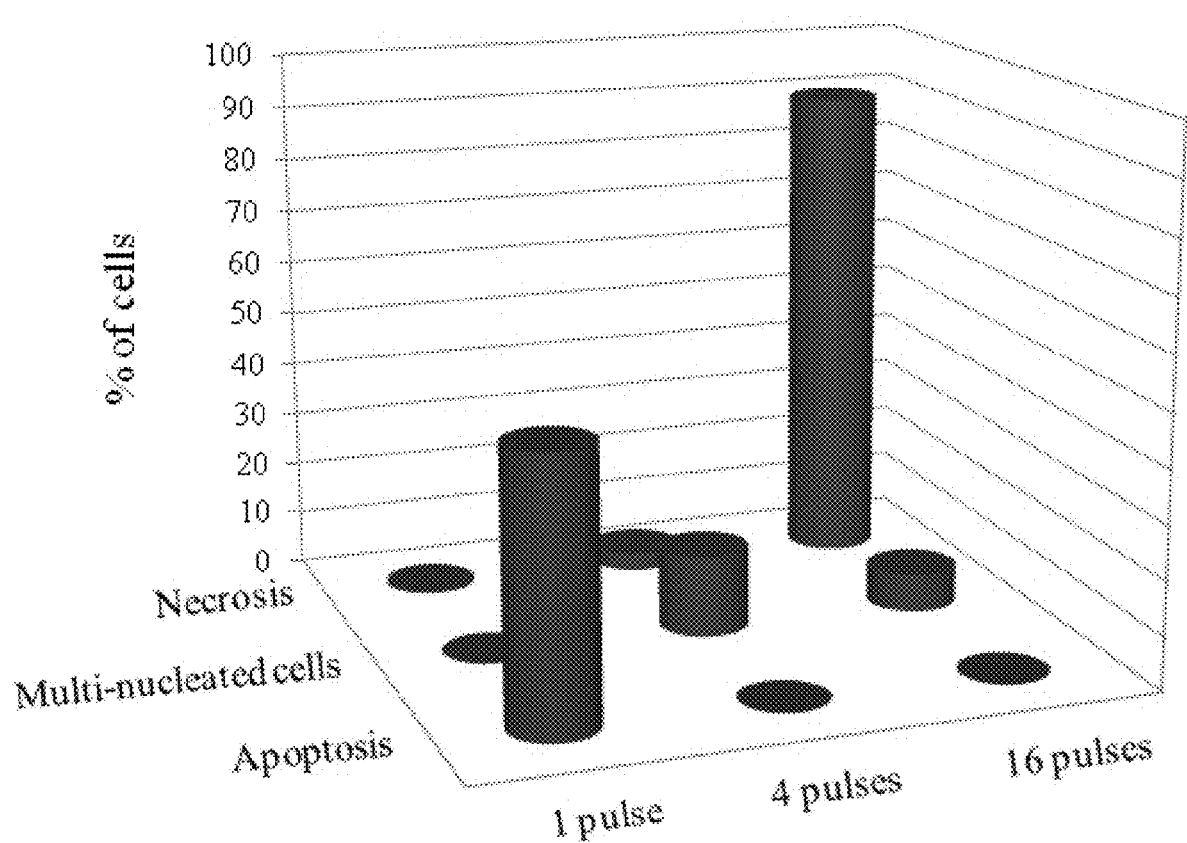

FIGS. 2A-B are schematic illustrations of an attachment process between a nanoparticles and cells;

FIG. 3 is a schematic illustration of a system suitable for inducing damage in a living cell according to some embodiments of the invention;

FIGS. 4A-B show the effect of interaction between gold nanospheres and the optical field, as obtained according to some embodiments of the invention;

FIGS. 5A-B show results of simulations performed according to some embodiments of the present invention for investigating near field enhancement;

FIGS. 6A and 6B are bar graphs summarizing results of a cancer cells experiment performed in accordance with some embodiments of the present invention;

FIG. 7 is a schematic illustration of an experimental setup, used in experiments performed according to some embodiments of the present invention;

FIGS. 8A-C show two-photon fluorescence images of carcinoma (A431) cells incubated according to some embodiments of the present invention with anti-EGFR coated gold nanoparticles (FIG. 8A), without nanoparticles (FIG. 8B), and with PEG-coated gold nanoparticles (FIG. 8C);

FIG. 8D shows scanning electron microscopy of a cell membrane targeted by anti-EGFR gold nanoparticles, as obtained during experiments performed according to some embodiments of the present invention;

FIG. 8E shows scanning electron microscopy using a back scattering detector as obtained during experiments performed according to some embodiments of the present invention;

FIGS. 9A-F show results of experiments performed according to some embodiments of the present invention for manipulating carcinoma cells (A431);

FIG. 10 shows percentage of cells undergoing necrosis (red bars), fusion (blue bars) and apoptosis (green bars) as a function of the number of irradiating pulses;

FIGS. 11A1-11A8, 11B and 11C show the effect of irradiation according to some embodiments of the present invention for specifically targeted lymphoma B cells;

FIGS. 12A1-12A6 and 12B1-12B6 shows time sequence fluorescence images obtained during experiments performed according to some embodiments of the present invention with non-specific gold nanoparticles;

FIGS. 13A-H show fluorescence activated cell sorting analysis of lymphoma B cells following laser irradiation;

FIGS. 14A-D are images obtained in experiments directed to investigate fusion specificity to EGFR-expressing cells;

FIGS. 15A-D are images obtained in experiments directed to investigate necrosis specificity to EGFR-expressing cells; and FIGS. 16A-F are images (FIGS. 16A, 16B, 16D and 16E) and plots (FIGS. 16C and 16F) obtained in experiments directed to investigate specific induction of necrosis in B-cells.

DESCRIPTION OF SPECIFIC EMBODIMENTS OF THE INVENTION

The present invention, in some embodiments thereof, relates to cell manipulation and, more particularly, but not exclusively, to light induced cell manipulation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

A method according to some exemplary embodiments of the present invention manipulates a living cell by rapidly heating a nanoparticle being attached to or in close proximity to the cell to induce one or more cell modifications.

In some embodiments of the present invention the cell modification comprises cell-damage, some embodiments of the present invention the cell modification comprises cell-fusion, As used herein the phrase "cell-damage" refers to the reduction in viability of a cell. In some embodiments of the present invention the cell-damage includes destruction of the cell.

As used herein the phrase "cell-fusion" refers to the merging, (either ex vivo or in vivo) of two or more viable cells.

The heating of the nanoparticle optionally and preferably results in formation of cavitation at or near a surface of the nanoparticle. The cavitation is optionally manifested by nanobubbles at or near a surface of the nanoparticle. In some embodiments of the present invention cell-damage or cell-fusion is induced by generating a pressure wave in the cell.

The cell may form any part of the human body, for example, an organ or a part of an organ, e.g., a blood vessel or part thereof, a tumor (malignant or benign) and any other pathological tissue, e.g., a restenotic tissue.

The method can be executed in-vivo, for example, by inserting a light transmitting device into the body of a living subject having the cell therein and directing an optical field to the nanoparticle such as to rapidly heat the particle.

The method can alternatively be executed ex-vivo (e.g., in-vitro) by directing an optical field to the particle while the particle and cell are placed on a carrier substrate or in a suitable chamber (e.g., a well of a multi-well plate) outside the body.

Execution of the method in-vivo is particularly useful when it is desired to damage the cell, and execution of the method ex-vivo is particularly useful when it is desired to induce cell-fusion.

Representative examples for cells that can be manipulated by the method and system of the present embodiments include, without limitation, primary cells and immortalized cells, identical cells and non-identical cells, human cells and non-human cells.

The phrase "immortalized cells" refers to cells or cell lines that can be passed in cell culture for several generations or indefinitely. An example of an immortalized cell is a tumor cell.

More specific examples for cells that can be manipulated by the method and system of the present embodiments include, without limitation, cancer cells (e.g., breast cancer cells, colon cancer cells, epidermoid carcinoma cells, Burkitt lymphoma cells, ovarian cancer cells, acute lymphoblasic leukemia cells, melanoma cells, pancreatic cancer cells), T-cells, helper T cells, inducer T cells, immature T cells, thymocytes, NK killer cells, suppressor T cells, B cells, activated B cells, dendritic cells, myeloid cells, plasma cells, endothelial cells, epithelial cells and glial cells. Other types of cells are not excluded from the scope of the present invention.

Figure 1:
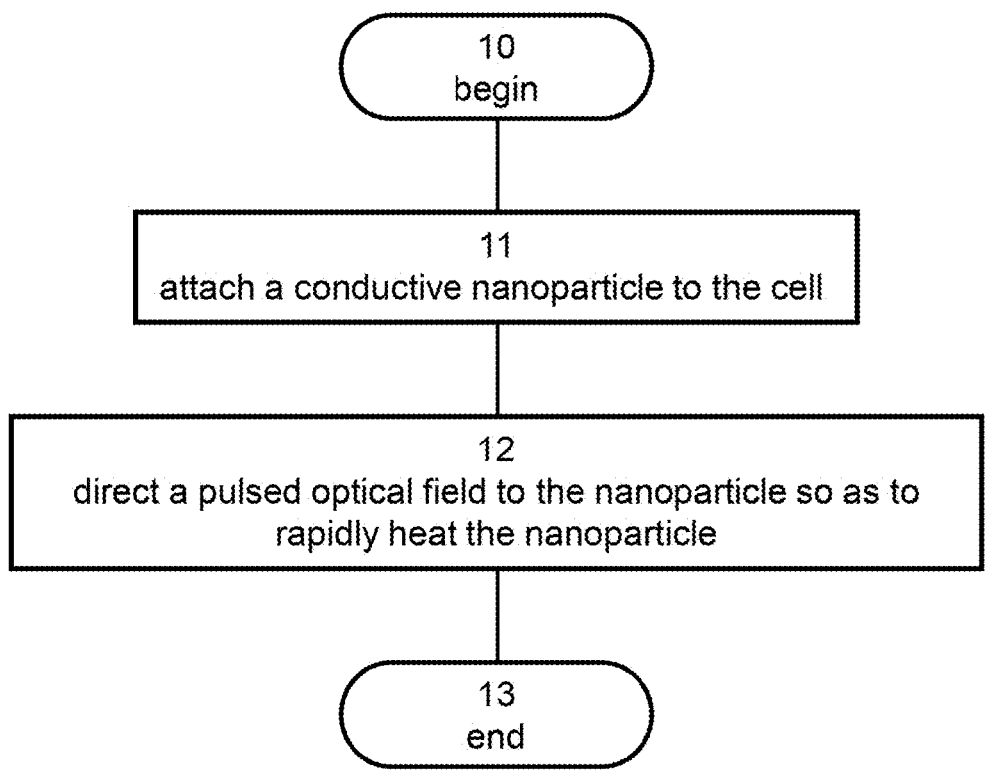

FIG. 1 is a flowchart diagram of the method according to some embodiments of the invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continues to 11 at which one or more conductive nanoparticles are attached to the cell. The nanoparticle(s), can be for example, a metal nanoparticle, preferably biocompatible metal nanoparticle, e.g., a gold nanoparticle. Gold nanoparticles are suitable markers in biotechnological systems because specific activities of micro-molecules can be retained when coupling micro-molecules to gold nanoparticles. In addition, gold nanoparticles can be easily visualized by electron microscopy. Since gold is inert, gold nano-particles are highly biocompatible. Representative examples of other metal nanoparticles suitable for the present embodiments including, without limitation, noble metals, silver, copper, platinum, palladium, lead, iron or the like. Alloys or non-homogenous mixtures of such metals can also be used.

The nanoparticles can be of any shape and structure, including, without limitation, spherical shape, rod shape, core-shell structure, cage structure and branched structure. In various exemplary embodiments of the invention the nanoparticles have a generally spherical shape, and in various exemplary embodiments of the invention the nanoparticles are solid. Optionally and preferably the nanoparticles have a generally spherical shape and are solid. It was found by the inventors of the present invention, that spherical and solid nanoparticles are advantageous since they are more stable to a pulsed optical field, as further detailed hereinunder.

The term "solid" in the present context refers to the union of the external surface of the shape with the volume enclosed or partially enclosed by that external surface. For example, a solid sphere of radius R is the union of the external surface of the sphere (defined in a Cartesian coordinate system by the equality $x^2+y^2+z^2=R^2$) with the anterior of the sphere (defined in a Cartesian coordinate system by the inequality $x^2+y^2+z^2<R^2$). Thus, a solid sphere is the geometrical object that is defined in a Cartesian coordinate system by the inequality $x^2+y^2+z^2 \leq R^2$. Such geometrical object is referred to mathematically as a ball.

The nanoparticle(s) may include an affinity component, whereby the affinity component has affinity to the living cell to be manipulated. The nanoparticle optionally and preferably has a diameter which is less than 100 nm or less than 50 nm, or less than 40 nm or less than 30 nm, e.g., about 20 nm.

As used herein, the term about refers to ±10%.

The affinity component of the particle facilitates the attachment of particle to the cell, preferably the cell's membrane, but attachments to other parts of the cell (e.g., nucleus, nucleolus, mitochondria, DNA, RNA, proteins etc.) is not excluded from the scope of the present invention.

In some embodiments, the affinity component comprises a moiety such as, but not limited to, an antibody, an antigen, a ligand or a substrate. The techniques of attaching proteins and other chemicals, to the surfaces of metal nanoparticles, are well known in the art. To this end, see, e.g., C. Zhang et. al., *Anal. Chem.* 74, 96 (2002); J. Ni et. al. *Anal. Chem.* 71, 4903 (1999); L. Lyon, et. al., *Anal. Chem.* 70, 5177 (1998), the contents of which are hereby incorporated by reference.

A representative of an attachment process in an embodiment wherein the affinity component is an antibody that is specific to an antigen on a target cell is illustrated in FIG. 2A. A nanoparticle 28 is conjugated with an antibody 26 which is specific to an antigen 24 of a target cell 20 (a cancer cell in the present example). A non-targeted cell (normal cell in the present example) that does not include antigen 24 is shown at 22. As shown, nanoparticle 28 is attached only to the target cell but not to the non-target cell, thereby ensuring specific attachment.

The following lists some primary antibodies known to specifically bind their associated cytological markers and which are presently employed as affinity components in immunohistochemical stains used for research and, in limited cases, for diagnosis and therapy of various diseases. Anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, and anti-Tn-antigen antibody (colon carcinoma, adenocarcinomas, and pancreatic cancer).

Also contemplated, are embodiments in which the nanoparticles are prepared so as to specifically target two or more types of cells. In these embodiments, a nanoparticle is preferably conjugated with two or more antibodies which are respectively specific to two or more antigens of respective two or more target cells. Thus, via the antibodies on its surface, the nanoparticle binds to two or more types of cells such that the two (or more) cells are maintained at close proximity to each other by virtue of their binding to same nanoparticle. A representative example of this embodiment is illustrated in FIG. 2B, showing nanoparticle 28 conjugated two antibodies 26a and 26b which are specific to two antigens 24a and 24b of two target cells 20a and 20b. Cell 20a is attached to nanoparticle 28 via the binding between antigen 24a and antibody 26a, and cell 20b is attached to the same nanoparticle 28 via the binding between antigen 24b and antibody 26b.

These embodiments are particularly useful when it is desired to bring two or more cells in a medium into close proximity with one another. For example, when it is desired to effect cell-fusion between two cells, the nanoparticles can be conjugated with more than one affinity component such that two or more cells are attached to the same nanoparticle. Such proximity between the cells enhances the rate of fusion between the cells.

While the embodiments above are described with a particular emphasis to nanoparticles that are attached to the cell (e.g., by means of an affinity component on the external surface of the nanoparticles), it is to be understood that more detailed reference to such targeting nanoparticles is not to be interpreted as limiting the scope of the invention in any way. The present inventors found that the method of the present embodiments is useful also when the nanoparticles are non-targeting, namely when the nanoparticles do not have specific affinity to the cells of interest.

The method continues to 12 at which a pulsed optical field (e.g., laser light) is directed to the nanoparticle so as to rapidly heat (e.g., at a rate of 10 or 20 or 30 or 40 or 50 or 100 degrees per nanosecond) the nanoparticle. Preferably, the heating is such that cavitations are generated at or near a surface of the nanoparticle. Cavitations can be generated by selecting a pulse duration which is much shorter than the heat diffusion from the nanoparticle to its surrounding. This results in heating of a thin liquid layer in the immediate vicinity (a few nanometers) of the surface of the particle, causing rapid evaporation. Optionally, the evaporation results in formation of nanobubbles. In some embodiments of the present invention the pulsed optical field is selected so as to generate a pressure wave (e.g., a pressure shockwave) in the cell.

It was found by the inventors of the present invention that a pulsed optical field results in rapid temperature elevation of the nanoparticle which induces expansion particle and the emission of a pressure wave, which may also be a pressure shockwave. The pulsed optical field is preferably selected to effect expansion of the nanoparticle by 0.1-0.5% in radius.

The aforementioned thermal effect is optionally and preferably the dominant effect in the manipulation (damage, fusion) of the cell. Another effect can be ionization of the cell.

As used herein, an effect X is said to be a "dominant effect" over another effect Y if effect X has a measurable extent which is at least two times or at least three times or at least four times or at least five times or at least ten times larger than a measurable extent of effect Y.

Thus, in various exemplary embodiments of the invention the thermal effect dominates the ionization effect. The measurable extent of these two effects can be the number of cells that are successfully manipulated (e.g., damaged, fused) by the respective effect. Thus, denoting the number of cells that are damaged by the aforementioned thermal effect, by $n_s$, and the number of cells that are damaged and/or fused by ionization effect by $n_i$, the ratio $n_i/n_s$ is preferably at least R, where R equals 2 or 3 or 4 or 5 or 6 or 7 or 8 or 9 or 10. For example, in some embodiments R=20 or more. In some embodiments of the present invention the heat is generated at the nanoparticle while preventing cell ionization. Thus, in these embodiments $n_i$ is approximately 0.

It was found by the present inventors that shorter pulses induce more ionization and less thermal effects and vice versa. Thus, in various exemplary embodiments of the invention the pulse duration is sufficiently long such that the ratio $n_i/n_s$ is at least R. Pulse duration suitable for the present embodiments can be, without limitation, in the picoseconds or femtoseconds time scale. In various exemplary embodiments of the invention the pulse duration is from about 6 fs to about 10 ns or from about 100 fs to about 10 ns or from about 1 ps to about 1 ns.

Reducing or eliminating the extent of the ionization allows controlling the type of manipulation caused to the cell. In some embodiments of the present invention the pulsed optical field is selected to damage the cell by apoptosis, in some embodiments of the present invention the pulsed optical field is selected to damage the cell by necrosis and in some embodiments of the present invention the pulsed optical field is selected to fuse cells. It was found by the inventors of the present invention that the type of manipulation can be controlled by a judicious selection of the number of pulses that are directed to the nanoparticle. Specifically, small number of pulses induces apoptosis, intermediate number of pulses induces cell-fusion, and large number of pulses induces necrosis.

In some embodiments of the present invention a set of pulse number thresholds is employed to define the appropriate number of pulses for the desired manipulation. Thus, for example, the method can employ three pulse number thresholds $N_1$, $N_2$ and $N_3$ ($N_1 < N_2 < N_3$), each being a positive integer. When it is desired to induce apoptosis, the number N of pulses that are applied satisfies $0 < N \leq N_1$, when it is desired to induce cell-fusion, the number N of pulses that are applied satisfies $N_1 < N \leq N_2$, and when it is desired to induce necrosis, the number N of pulses that are applied satisfies $N_2 < N \leq N_3$.

Typical values for the threshold $N_1$ include, without limitation, $N_1=1$ or $N_1=2$ or $N_1=3$, typical values for the threshold $N_2$ include, without limitation, any integer from 3 to 10, and typical values for the threshold $N_3$ include, without limitation, any integer from 10 to 20, with the provision that $N_1 < N_2 < N_3$. These values are particularly useful for pulses having a pulse duration of from about 10 fs to about 200 fs (e.g., 50 fs), a pulse repetition rate of from about 500 Hz to about 2 kHz (e.g., 1 kHz), and energy density from about 10 mJ/cm² per pulse to about 50 mJ/cm² per pulse (e.g., 35 mJ/cm² per pulse).

It is appreciated that the above manipulation effects may be immediate or they may occur some time (e.g., from about 2 hours to about 48 hours) after the irradiation. During this time period, the cells are optionally and preferably not irradiated by the optical field. For example, cell-fusion and necrosis may occur to an identifiable extent 3-7 hours following the irradiation, and apoptosis may occur to an identifiable extent at least 20 hours following the irradiation. Other time-periods are not excluded from the scope of the present invention.

The peak-power of the optical field is preferably smaller than the ionization threshold of the cells, which threshold is typically from about $10^{10}$ Watts/cm² to about $10^{14}$ Watts/cm². The average irradiance and/or fluence of the optical field is preferably below the heating damage threshold for bodily tissues. The use of peak-power which is below ionization threshold and average intensity of which is below the heating damage threshold prevents or reduces global cell destruction across the entire illumination area, along its efficient penetration depth.

Typical repetition rates of the pulsed optical field which are suitable for the present embodiments are less than 10 kHz (namely less than 10,000 pulses per second), e.g., from about 500 Hz to about 2 kHz, or from about 500 Hz to about 1500 Hz, or from about 800 Hz to about 1200 Hz. In some embodiments of the present invention a single pulse is applied. Also contemplated are embodiments in which the pulsed optical field has a sub-Hertz repetition rate.

When the nanoparticles are irradiated by the optical field, there is a substantial local increment of the optical field near the particles, which increment is larger for smaller particles. The physical process of strong field enhancement very close to metal nanoparticles is a well known phenomenon and has been described in detail in the literature. To this end, see, for example, R. H. Doremus and P. Rao, *J. Mater. Res.*, 11, 2834 (1996); M. Quinten, *Appl. Phys. B* 73, 245 (2001) and R. D. Averitt, S. L. Westcott and N. J. Halas, *J. Opt. Soc. Am. B* 16, 1824 (1999), the contents of which are hereby incorporated by reference.

In metal nanoparticles, resonant collective oscillations of conduction electrons, also known as particle plasmons, are excited by an optical field. The resonance frequency of a particle plasmon is determined mainly by the dielectric function of the metal, the surrounding medium and by the shape of the particle. Resonance leads to a narrow spectrally selective absorption and an enhancement of the local field confined on and close to the surface of the metal particle. The spectral width of absorption and near-field enhancement depends on the decay time of the particle plasmons.

The wavelength of the optical field is preferably the same or similar (e.g., within 10%) as the plasmon resonance frequency of the nanoparticle. It was found by the inventors of the present invention that with such selection the local electric field in proximity to the nanoparticle is enhanced by 2 or more orders of magnitude.

In various exemplary embodiments of the invention the wavelength of the optical field is from about 520 nm to about 580 nm, e.g., about 532 nm or about 550 nm. These embodiments are particularly useful when the nanoparticles are solid nanospheres, about 20 nm in diameter.

Also contemplated is the use of nanoparticles which include a dielectric core and a conducting shell layer. Nanoparticles having such structure are called nanoshells. The dielectric core or dielectric core layer may be, for example, a semiconductor material, an organic molecule, an organic super-molecular structure, or any mixture of non-conducting materials. Optionally, the non-conducting core layer may include an optically absorbing material, and/or a fluorescent material.

Nanoshells are particularly useful in cases of near infrared wavelengths, but they may also be used for short wavelengths applications. The process of manufacturing nanoshells having a dielectric core and a conducting shell, is known in the art and is described in, for example, WO 01/06257 and WO 02/28552, the contents of which are hereby incorporated by reference. For any given core and shell materials, the ratio between the core radius and the total radius of nanoshells can be chosen for maximum scattering and minimum absorption at a specific resonance frequency. Based on the core to total radii ratios, the nanoshells manifesting plasmon resonances extending from ultraviolet to infrared can be readily fabricated. Hence, the core diameters of the nanoshells may range from about 1 nm to about 400 nm or more, and the shell thickness may range from about 1 nm to about 100 nm. For a near infrared light, the total diameter of the nanoshells may be reduced down to 20 nm.

Suitable metals for forming the outer layer of the nanoshells include, without limitation, any of the aforementioned metals. Suitable dielectric core materials for the nanoshells include, without limitation, silicon dioxide, goldsulfide, titanium dioxide, polymethyl methacrylate (PMMA), polystyrene, and macromolecules such as dendrimers. The core of the nanoparticle may also be a combination or a layered combination of dielectric materials such as those listed above.

While the use of nanoshells is not excluded from the scope of the present invention, the present inventors found that solid nanospheres are preferred from the standpoint of particle-stability. Specifically, solid nanospheres can sustain more optical pulses at their resonance wavelength compared to hollow particles or particles having a core made of a softer material or particles having a non-spherical shape.

The method ends at 13.

A system 30 suitable for performing at least some operations of the method is illustrated in FIG. 3. System 30 comprises an optical device 34 for providing a pulsed optical field. System 30 can also comprise a controller 40 configured for selecting at least one parameter of the optical field so as to effect at least one cell modification selected from the group consisting of cell-damage and cell-fusion. In various exemplary embodiments of the invention the parameter(s) is selected from the group consisting of the number of pulses, the duration of the pulses, and repetition rate of the pulsed optical field according to the desired manipulation of the cells, as further detailed hereinabove. System 30 optionally and preferably also comprises a plurality of nanoparticles 28 as further detailed hereinabove.

In some embodiments of the present invention system 30 comprises optical element 38 for focusing the optical field onto the volume occupied by the nanoparticles. Optical element 38 may be any known element for focusing (e.g. collimating) an optical beam, such as, but not limited to a converging lens. The optical device 34 optionally and preferably comprises a waveguide 36, e.g., fiber optic bundle, for guiding the optical pulses into a body of a subject. The waveguide has an emission face, through which the optical pulses are emitted to the living cells. System 30 device may be used either in an invasive medical procedure or in non-invasive medical procedure. In any case, the waveguide is preferably sterile. The sterilization of the waveguide may be, for example by a disposable sterile coat, which covers at least a portion of the waveguide.

The present invention successfully provides a light-induced cell-fusion procedure. The procedure can includes selected operations of the method described above with reference to FIG. 1. The selected operations can be executed using system 30.

Optionally, but not necessarily, the cell-fusion procedure is executed in the presence of nanoparticles and cells such that at least one nanoparticle is attached to two or more cells, thereby maintaining a proximity between these two or more cells. The attachment can be via affinity components selected to facilitate the attachment of the nanoparticle to the cells to be fused. Also contemplated are embodiments in which the cell-fusion procedure is executed in the presence of nanoparticles and cells, wherein nanoparticles are attached to no more than one cell per nanoparticle, and embodiments in which the nanoparticles are non-targeting, namely when the nanoparticles do not have specific affinity to the cells of interest.

The cell-fusion procedure of the present embodiments can be used, for example, to assist in the ex vivo fusion between tumor cells and antibody producing cells (e.g. B lymphocytes) to produce a hybridoma.

The term "hybridoma" as used herein refers to a cell that is created by fusing two cells, an antibody secreting cell from the immune system, such as a B-cell, and an immortal cell, such as a myeloma, within a single membrane. The resulting hybrid cell can be cloned, producing identical daughter cells. Each of these daughter clones can secrete cellular products of the immune cell over several generations.

According to some embodiments of the present invention, the B lymphocytes are human B lymphocytes. In some embodiments, the B lymphocytes are those which circulate in the peripheral blood e.g. PBMCs. In some embodiment, the B lymphocytes are murine splenic B cell.

Examples of tumor cells which may be used to produce hybridomas according to the present embodiments include, without limitation mouse myeloma cells and cell lines, rat myeloma cell lines and human myeloma cell lines.

Optionally and preferably, the myeloma cell lines comprise a marker so a selection procedure may be established. For example the myeloma cell lines may be HGPRT negative (Hypoxanthine-guanine phosphoribosyl transferase) negative. Specific examples thereof include: X63-Ag8 (X63), NS1-Ag4/1(NS-1), P3X63-Ag8.UI(P3UI), X63-Ag8.653(X63.653), SP2/0-Ag14(SP2/0), MPC11-45.6TG1.7(45.6TG), FO, S149/5XXO.BU.1, which are derived from mice; 210.RSY3.Ag.1.2.3(Y3) derived from rats; and U266AR(SKO-007), GM1500 GTG-A12 (GM1500), UC729-6, LICR-LOW-HMy2(HMy2), 8226AR/NIP4-1 (NP41) and MFP-2, which are derived from humans.

In some embodiments of the present invention, the tumor cells and/or B lymphocytes are incubated in a medium (e.g., a culture medium) prior to during and/or following the light-induced cell-fusion procedure.

As used herein the phrase "culture medium" refers to a medium having a composition which allows eukaryotic cells to remain viable for at least 12 hours and preferably to replicate.

The cell-fusion procedure of the present embodiments can be used to aid in the ex-vivo or in-vivo fusion between other cells such as tumor cells and dendritic cells. Dendritic cells are potent antigen-presenting cells, and can induce effective cytotoxic T-lymphocyte-dependent anti-tumor immunity. Dendritic cells are found throughout the body, and include cutaneous epidermal Langerhans cells, dermal dendritic cells, dendritic cells located in the lymph nodes and spleen, and dendritic cells derived through in vitro culture of precursors. Procedures are available to obtain significant quantities of dendritic cells, e.g., from bone marrow or peripheral blood derived precursors.

The cell-fusion procedure of the present embodiments can also be used to aid in the in vivo fusion between somatic cells and stem cells. Because of their powerful generative and regenerative abilities, stem cells may be used to repair damage in the bone marrow and to different organs such as the liver, brain and heart. It has been shown that some of the stem cells' repair properties come from their ability to fuse with cells that are naturally resident in the organs they are repairing [Wang et al., 2003, Nature 422, 897-901]. Accordingly, cell-fusion procedure of the present embodiments can be used to enhance fusion between stem cells and somatic cells such as bone cells and muscle cells.

The cell-fusion procedure of the present embodiments can also be used for in vivo transferring nucleic acids.

Another ex vivo process which may be aided by the light-induced cell-fusion of the present embodiments is the fusion between embryonic stem cells and human cells. Such fusions were shown to generate hybrids which behaved in a similar manner to embryonic stem cells, thus generating genetically matched stem cells for transplants. Specifically, human embryonic stem (hES) cells were fused with human fibroblasts, resulting in hybrid cells that maintain a stable tetraploid DNA content and have morphology, growth rate, and antigen expression patterns characteristic of hES cells [Cowan et al., Science, Aug. 26, 2005; 309(5739):1369-73].

Another ex vivo process which may be aided by the light-induced cell-fusion of the present embodiments is somatic cell nuclear transfer. This is the process by which a somatic cell is fused with an enucleated oocyte. The nucleus of the somatic cell provides the genetic information, while the oocyte provides the nutrients and other energy-producing materials that are necessary for development of an embryo. This procedure can be used for cloning and generation of embryonic stem cells.

The light-induced cell-fusion of the present embodiments can optionally and preferably be performed in the presence of a fusion stimulus such as, but not limited to, polyethylene glycol (PEG) or Sendai virus (See, for example, Harlow & Lane (1988) in Antibodies, Cold Spring Harbor Press, New York).

The present embodiments also contemplate a method of monoclonal antibody production including the light-induced cell-fusion described above and the cloning of hybridomas generated thereby.

As used herein, the phrase "monoclonal antibody" refers to an immune molecule that comprises a single binding affinity for any antigen with which it immunoreacts.

According to the present embodiments, monoclonal antibodies are generated by fusing an immortalizing cell with an antibody producing cell to produce hybridomas.

The generated hybridomas are then be cloned, for example, by incubating single hybridomas in a suitable medium.

Following generation of hybridomas and optional cloning thereof, monoclonal antibodies may be screened and harvested. Many methods of screening are known in the art including functional and structural assays. An exemplary method for screening hybridomas includes the use of ELISA assay. Techniques for harvesting of monoclonal antibodies are also well known in the art and typically comprise standard protein purification methods.

The present invention successfully provides an ablative procedure for destroying living cells present in a body of a subject. The ablative procedure includes the following operations, which may be executed, of the present embodiments using system 30. A plurality of particles is administrated to the body of the subject. The particles can be similar to the nanoparticles described hereinabove. A pulsed optical field is then directed toward the nanoparticles, to rapidly heat the nanoparticles as further detailed hereinabove. The pulsed optical field can be directed using a light transmitting device which may inserted into the body of the subject. The light transmitting device may be any device known in the art, e.g., a fiber optic bundle. The light transmitting device can be inserted into the body by either endoscopy or laparoscopy. The ablation procedure may be executed in parallel to another surgical procedure, while the unwanted cells of the subject are exposed.

In any of the above embodiments, the living cell to be destroyed may form a part of a tumor, selected from the group consisting of a breast tumor, brain tumor, neuroblastoma, thyroid gland tumor, gestational trophoblastic tumor, uterine sarcoma, carcinoid tumor, colon carcinoma, esophageal carcinoma, hepatocellular carcinoma, liver carcinoma, lymphoma, plasma cell neoplasm, mesothelioma, thymoma, alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, synovial sarcoma, melanoma, neuroepithelioma, osteosarcoma, leiomyosarcoma, Ewing sarcoma, osteosarcoma, rhabdomyo-sarcoma, hemangiocytoma, myxosarcoma, mesothelioma (e.g., lung mesothelioma), granulosa cell tumor, the coma cell tumor and Sertoli-Leydig tumor.

Hence, the present embodiments can be used to treat many types of cancers, such as, but not limited to, vaginal cancer, vulvar cancer, cervical cancer, endometrial cancer, ovarian cancer, rectal cancer, salivary gland cancer, laryngeal cancer, nasopharyngeal cancer, many lung metastases and acute or chronic leukemia (e.g., lymphocytic, Myeloid, hairy cell).

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Embodiments of the present invention have been utilized for cell modulation.

Example 1

Cell Destruction

Materials and Methods

The optical field was generated by an amplified titanium sapphire laser system (Spectra Physics (Newport copr.) whose wavelength was modified by means of an optical parametric amplification (OPA). The optical field was characterized by the following parameters: wavelength of 550 nm, pulse duration of 50 fs and pulse repetition rate of 1 kHz. The resulting fluence was approximately 0.35 J/cm$^2$ (0.7 TW/cm$^2$ irradiance). The number of pulses was from 1 to 16.

The nanoparticles were gold nanospheres attached to an anti-EGFR antibody. The target cells were A431 cancer cells. The following protocol was employed. Anti-EGFR coated gold nanoparticles were incubated with the cell culture at a final concentration of 1.5×10$^{11}$ particles/ml for 1 hour at 37° C. Following incubation, the unbound nanoparticles were washed off the cells using 3 consecutive washes with physiological medium. Before irradiation, cells were reimmersed in cell growth medium.

Results

FIGS. 4A-B show the effect of interaction between the gold nanospheres and the optical field, where FIG. 4A corresponds to gold nanospheres having diameter of 16 nm and FIG. 4B corresponds to gold nanospheres having diameter of 45 nm. Shown in FIGS. 4A-B are theoretical calculations (dashed lines) and experimental measurements (solid lines) of the extinction (absorption and scattering) in units of mm$^{-1}$ as a function of the wavelength. As shown, for both average diameters, the plasmon resonance wavelength is measured to be approximately 530 nm.

FIGS. 5A-B show results of simulations directed to the investigation of near field enhancement. FIG. 5A shows the enhancement map for 60 nm nanospheres (z is parallel to the direction of the wave vector k, and x orthogonal to the wave vector), and FIG. 5B shows the maximum enhancement for various wavelengths and nanosphere diameters, indicating resonance wavelengths in the range of 520-580 nm for particle diameters smaller than 100 nm, where the maximum intensity enhancement is 100× for 60 nm particles at a wavelength of 550 nm.

FIGS. 8A-C are 2-photon fluorescence images of the A431 cell culture, where FIG. 8A is a control culture, FIG. 8B is the culture in the presence of PEG coated nanospheres (without affinity component), and FIG. 8C is the culture in the presence of nanospheres conjugated with anti-EGFR antibody. The images were obtained after a 60 minutes incubation. As shown, there is a specific binding between the antibody-nanosphere conjugates and the cells.

Figure 9:
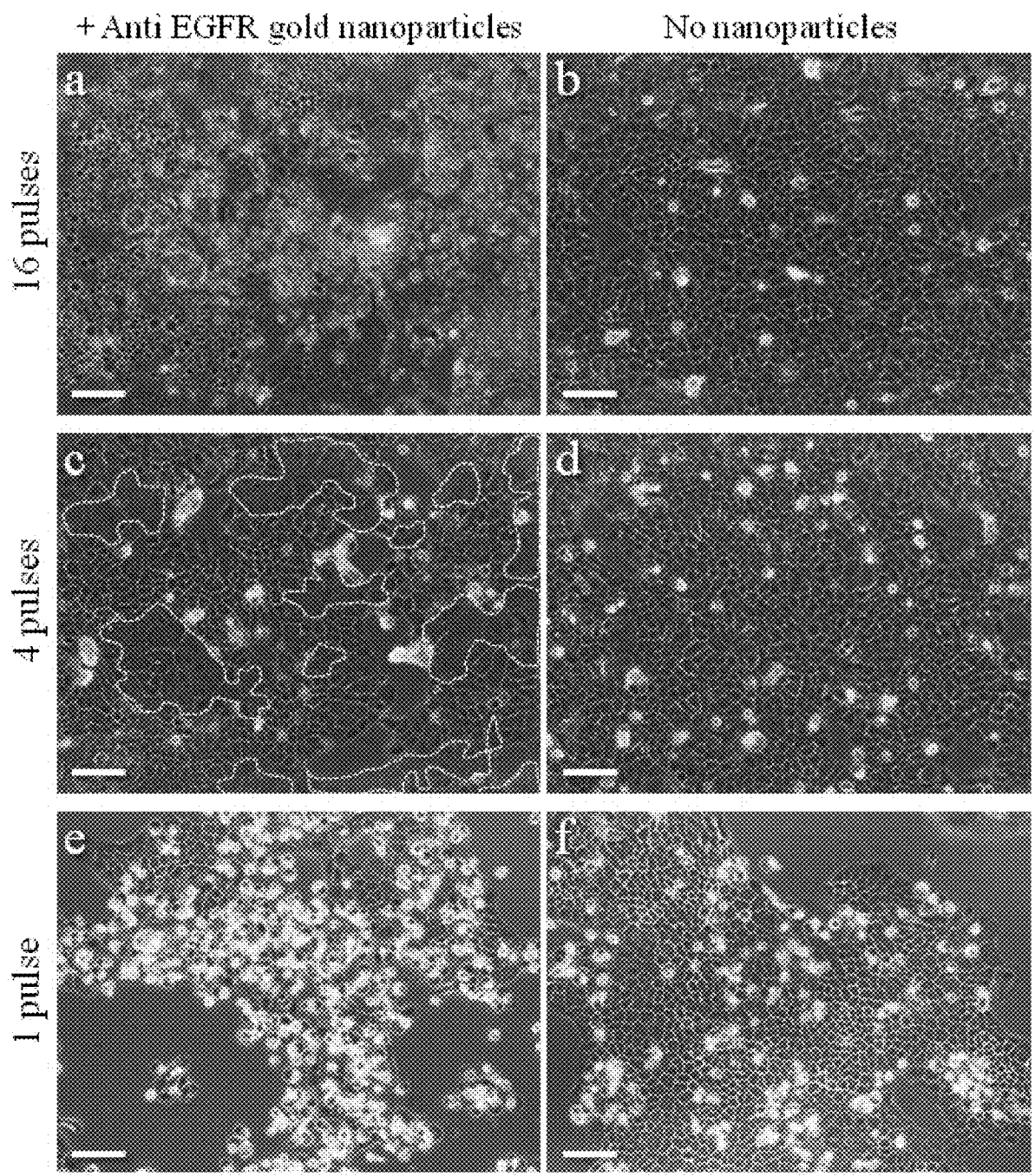

FIGS. 9A, 9B, 9E and 9F are combined phase contrast and fluorescence images of the A431 cell. The fluorescence markers are Annexin V (green), labeling apoptotic cell, and Propidium iodide (red) labeling necrotic cells. FIG. 9E is the control culture with no nanoparticles, illuminated by 1 pulse and imaged 23 hours after illumination. FIG. 9F is a culture incubated with anti-EGFR coated nanoparticles, illuminated by 1 pulse and imaged 5 hours after illumination. FIG. 9A is the control culture with no nanoparticles, illuminated by 16 pulse and imaged 5 hours after illumination. FIG. 9B is a culture incubated with anti-EGFR coated nanoparticles, illuminated by 16 pulses and imaged 5 hours after illumination. As shown, the lack of nanoparticles caused no visible damage, irradiation by 1 pulse induced mainly apoptosis and irradiation by 16 pulses induced necrosis.

FIGS. 6A and 6B are bar graphs summarizing the results of the A431 cancer cells experiment. Light-induced necrosis cases are summarized in and light-induced apoptosis cases are summarized in FIG. 6B. As shown in FIG. 6A, necrosis was observed in cells that were attached to nanoparticles and irradiated by 16 pulses. As shown in FIG. 6B, apoptosis was observed in cells that were attached to nanoparticles and irradiated by 1 pulse.

Example 2

Cell Destruction and Cell Fusion

Materials and Methods
Experimental System

A schematic illustration of the experimental setup is illustrated in FIG. 7. The setup was a custom-built inverted microscope system which, using a single platform, allowed sample irradiation by single intense femtosecond pulses, two-photon excitation fluorescence microscopy, and time lapse multichannel fluorescence imaging A beam from an optical parametric amplifier (OPA) at wavelength 550 nm (green line) was scanning the sample using two scanning mirrors. A single lens (L1) was used to reduce the beam's diameter on the sample to 250-350 µm. For two-photon imaging, the beam from the Ti:Sapphire oscillator was picked using a flipped mirror (M), scanned and magnified using lenses L2 and L3, and focused by inserting an objective lens before the sample. The two-photon fluorescence signal was detected by a photo-multiplier tube (PMT) after replacing the high reflectivity (HR) mirror by a dichroic short-pass mirror (LP-700). After irradiation, time lapse imaging was conducted by replacing the dichroic mirror with different filter cubes optimized for the specific fluorescence markers. Shown in FIG. 1 are the irradiation pattern of the pulse beam (I), the irradiated nanoparticle-targeted cells (II), and the extent of the nanometric effect induced by each nanoparticle (III), including the near field enhancement beyond the ionization threshold (red regions), the spherical shock wavefront (gray sphere), and the affected area on the membrane (dashed circle).

Cell Cultures

A431 epidermoid carcinoma cells (ATCC) were grown in DMEM medium (Invitrogen) in 10% heat inactivated fetal bovine serum and 1 mM sodium pyruvate. BJAB and NSO cells were grown in RPMI-1640 medium (Sigma) supplemented with 2 mM glutamine and 5 mM sodium pyruvate. 10% heat-inactivated fetal bovine serum was added to BJAB cell culture and 10% heat-inactivated horse serum was added to NSO cell culture. BJAB and NSO cells were maintained at a concentration below $10^6$ cells per ml to allow logarithmic growth. All cells were grown at 37° C. and 5% $CO_2$ Nanoparticle Preparation Gold nanoparticles were prepared using a citrate reduction protocol[47, 48] resulting in average particle diameter of 20 nm. PEG coating was obtained by overnight incubation of the nanoparticles with $7.5\times10^{-3}$ mM PEG-Thioctic acid (PEG-TA; MW 2000; Jenkem) followed by three PBS washes of unbound PEG. Addition of $6.6\times10^{10}$ PEG-coated nanoparticles per ml to the growth medium of both carcinoma and lymphoma cells did not cause any visible effect (fusion, cell death) to the cells. Anti-CD20 (Rituximab, Roche Israel) coating of gold nanoparticles was carried out according to Weiss et al. [A. Weiss, T. C. Preston, J. Popov, Q. Li, S. Wu, K. C. Chou, H. M. Burt, M. B. Bally, R. Signorell, *The Journal of Physical Chemistry C* 2009, 113, 20252-20258], the contents of which are hereby incorporated by reference. Anti-EGFR (Lab Vision, clone designation EGFR.1) coated gold nanoparticles (20 nm average diameter) were custom made by Millennium Biotechnology Inc.

Cell Targeting by Nanoparticles

A431 cells (80-90% confluency) were incubated for 1 h at 37° C. with $1.5\times10^{11}$ anti-EGFR-coated gold nanoparticles per ml. BJAB cells ($10^6$ cells per ml) were incubated for 20 min at 37° C. with $4.5\times10^9$ Rituximab-coated gold nanoparticles per ml. Cells were washed off unbound gold nanoparticles (three PBS washes) prior to laser irradiation. Specific binding of the Rituximab-coated nanoparticles to the BJAB cells was verified using dark field microscopy. For experiments with nonspecific cell targeting, PEG-coated gold nanoparticles were used at a concentration of $6.6\times10^{10}$ per ml.

Fluorescence Labeling

Cells were stained for apoptosis and necrosis using Annexin V and Propidium iodide kit (Roche). For the fusion experiments, nuclei were stained with either DAPI at 2 μg/ml concentration (Sigma), Hoechst 33342 at 2 μg/ml (Sigma), or 10 mM Doxorubicin (Sigma). Cell membranes were stained using $2\times10^{-6}$ M PKH67 (Sigma).

Laser Pulse Irradiation

A beam from a Ti:sapphire oscillator (Tsunami, Spectra Physics) was amplified (Spitfire Pro XP, Spectra Physics) and wavelength-tuned to 550 nm using an optical parametric amplifier (Topas-C, Spectra Physics). Pulse duration was 50 fs, at 1 kHz repetition rate. Cells were irradiated within 8-well chamber slides (Lab-Tek II, Thermo-scientific) which were placed within a microscope incubator (Okolab Inc.) at controlled temperature and $CO_2$ concentration. Irradiation pattern was either a 10×10 rectangular array of 350 μm diameter spots (approximately 12 $mm^2$ total area) or a 35×35 rectangular array of 250 μm diameter spots (approximately 75 $mm^2$ total area) for the A431 and BJAB cell cultures, respectively. Multiple pulse irradiations per spot were achieved by scanning the beam at lower rates, so that each point was irradiated by several consequent overlapping spots.

Two Photon Microscopy

The beam from a Ti:sapphire oscillator (25 fs, 80 MHz, 800 nm) was scanned using two galvanometric scanners (Cambridge Technology), magnified and focused onto the sample using a 60×, NA=1.4 objective. Average power on the sample was approximately 16.5 mW. The two-photon excited fluorescence was filtered using a short-pass dichroic mirror (dcspxr700, Chroma technology) and a barrier filter (E680SP-2P, Chroma technology), and measured using a photomultiplier tube (H7422-40, Hamamatsu photonics). Each image represents a z-projection of a data cube which contains twenty 500×500 pixel frames, each captured at 0.5 μm intervals along the z axis. Acquisition time was 50 s per frame.

Time-Lapse Imaging

Time-lapse imaging was controlled using MS-Elements Advanced Research (Nikon) software. Frame rate was 3 per minute during the first 10 hours of each experiment, followed by a frame rate of 1 per hour during the rest of the imaging period.

Scanning Electron Microscopy

A431 cells were fixated using 3% Glutaraldehyde and 1% Osmium[50] on silicon chips (Ted Pella, Inc.). The microscope system used (Zeiss Ultra Plus HRSEM) was equipped with a Schottky field-emission electron gun and BalTec VCT100 cold-stage maintained at (−150° C.).

Data Analysis

Selected images of A431 cells acquired 5 h and 23 h after irradiation were used to quantitatively assess necrosis and apoptosis ratios using MS-Elements Advanced Research (Nikon) software. The ratio of damaged cells within each frame was measured for each set of irradiation parameters and normalized according to the corresponding control experiments. Cell fusion was evaluated by manually counting and segmentation of the fused cells. Selected images of BJAB cells 15 h after irradiation were used to evaluate necrosis percentage. Cell fusion rate was measured by manually counting the fusing cells using the entire time-lapse data sets. Quantification of necrosis in large populations of BJAB cells was conducted using fluorescence activated cell sorting (BD FACS Calibur), in which cells were first stained using 1 μg/μl propidium iodide and then detected using 488 nm excitation wavelength. Results were analyzed using cyflogic software (CyFlo Ltd).

Results

Biochemical targeting of gold nanoparticles to epidermoid carcinoma (A431) and Burkitt lymphoma B (BJAB) cells was attained using particles which were coated with anti-EGFR antibody and chimeric anti-CD20 monoclonal antibody (Rituximab TM), respectively.

FIG. 8A-C show carcinoma (A431) cells incubated with anti-EGFR coated gold nanoparticles (FIG. 8A), without nanoparticles (FIG. 8B), and with PEG-coated gold nanoparticles (FIG. 8C). The scale bars in FIGS. 8A-C represent 30 μm.

FIG. 8D shows scanning electron microscopy of a cell membrane targeted by anti-EGFR gold nanoparticles, and FIG. 8E shows scanning electron microscopy using the back scattering detector revealing bright reflections indicative of gold particles (marked by arrows). The scale bars in FIGS. 8D-E represent 100 nm.

Two-photon excitation fluorescence microscopy of the nanoparticle-targeted A431 cells showed strong fluorescence signals emitted from the gold nanoparticles which were attached to the cell membranes (FIG. 8A), while control cells without nanoparticles (FIG. 8B) or with non-specific (polyethylene glycol (PEG)-coated) nanoparticles (FIG. 8C) exhibited only a weak auto-fluorescence. Further confirmation of the specific binding of the nanoparticles-antibody conjugates to the cells was attained using scanning electron microscopy (SEM), which revealed small nanometric features on the cell membranes (FIG. 8D) and identified their high atomic number (FIG. 8E). The SEM images also revealed that nanoparticles were attached to the cells' membranes either as isolated individual particles, or in small aggregates (data not shown).

FIGS. 9A-F show results of experiments directed to manipulate carcinoma cells (A431), where FIG. 9A shows gold nanoparticle-conjugated cells irradiated by 16 pulses, FIG. 9B shows non-conjugated cells irradiated by 16 pulses, FIG. 9C shows conjugated cells irradiated by 4 pulses, FIG. 9D shows non-conjugated cells irradiated by 4 pulses, FIG. 9E shows conjugated cells irradiated by 1 pulse, and FIG. 9F shows non-conjugated cells irradiated by 1 pulse. Multi-nucleated cells margins are marked by white dashed curves in FIG. 9C. The scale bars represent 50 µm. Red nuclei indicate necrotic cells and green stain indicates apoptosis. FIGS. 9A-D show the cells 5 hours after irradiation, and FIGS. 9E and 9F show the cells 23 hours after irradiation.

The cells in FIGS. 9A-F were irradiated using 50 fs pulse beam whose wavelength (550 nm) was tuned to the plasmonic resonance of the nanoparticles. Widespread necrosis was evident in A431 cells which were incubated with anti-EGFR gold nanoparticles and irradiated by 16 pulses (35 mJ/cm$^2$ per pulse), 5 hours after irradiation (FIG. 9A). Control cells which were not incubated with nanoparticles and irradiated with an identical pulse series showed only a small amount of necrotic and apoptotic cells (FIG. 9B).

Nanoparticle-targeted cells irradiated by 4 pulses showed insignificant necrosis rate 5 hours after irradiation. Instead, numerous neighboring cells have began to fuse with each other, forming several giant multi-nucleated cells throughout the field of view (FIG. 9C). Control cells with no nanoparticles which were irradiated by 4 pulses have shown no such behavior (FIG. 9D).

Using only a single pulse irradiation, no significant effect was observed at the nanoparticle-targeted cells after 5 hours, however, the number of apoptotic cells increased significantly 23 hours post irradiation (FIG. 9E), in comparison to the control cells with no nanoparticles (FIG. 9F).

Large plasma membrane vesicles, or blebs, are noticeable in FIG. 9A, and to a lesser extent in FIGS. 9C and 9E, indicating the rupture of the cellular plasma membrane-cytoskeleton interface due to the combined effect of the pulse irradiation and the nanoparticles.

FIG. 10 shows the percentage of cells undergoing necrosis (red bars), fusion (blue bars) and apoptosis (green bars) as a function of the number of irradiating pulses. As shown, there is a strong correlation between the type manipulation and the number of pulses for irradiation. Nearly 90% of the cells became necrotic 5 hours following irradiation by 16 pulses, 15% of the cells were fused with nearby cells after 4 pulses, and 50% of the cells became apoptotic 23 hours after a single pulse irradiation.

Figure 8:
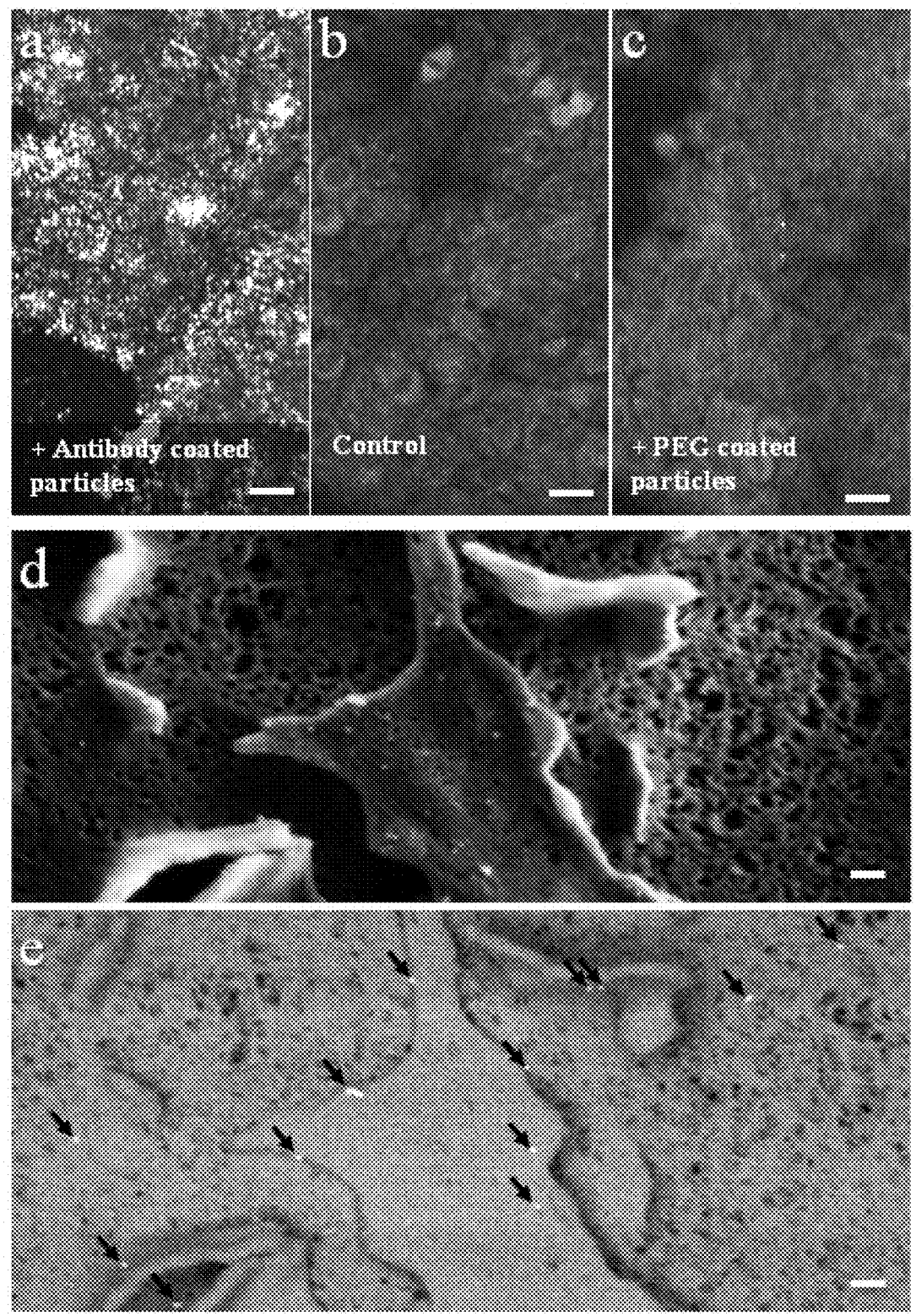

FIGS. 11A1-11A8, 11B and 11C show the effect of the irradiation for specifically targeted lymphoma B cells. FIGS. 11A1-A8 (including 8 panels) show fluorescence images of propidium iodide (indicating necrotic cells) distribution superimposed on phase contrast images, 15 hours following irradiation by sequences of 1, 4, and 16 pulses. The scale bars in FIGS. 11A1-11A8 represent 70 µm. FIG. 11B is a bar chart summarizing the percentage of necrotic cells in FIGS. 11A1-11A8, and FIG. 11C is a bar chart summarizing the percentage of necrotic and fused lymphoma BJAB cells irradiated by 16 pulses, as a function of increasing pulse fluence. The numbers of necrotic cells and fused cells were evaluated 15 hours and 1 hour post irradiation, respectively. The acronym GNP corresponds to gold nanoparticles.

The experiments with lymphoma B cells in suspension have revealed similar results to those obtained with the epidermoid carcinoma cells. Incubation with Rituximab-coated nanoparticles did not appear to significantly affect BJAB cell viability after 20 min incubation (no irradiation), as compared to the control BJAB cells with no nanoparticles (FIGS. 11A1-11A2, top panels). The Rituximab induced aggregation of the nanoparticle-targeted cells. Irradiation of nanoparticle-targeted cells by 1 and 4 pulses has led to approximately 25% and 60% necrotic cells in the culture, respectively, nearly five times the measured rates at cells with no nanoparticles (FIG. 11B). Increasing the number of irradiation pulses to 16 resulted in nearly 90% necrosis, independent of the presence of nanoparticles (FIGS. 11A7-11A8, bottom panels). FIG. 11B demonstrates that the gold nanoparticles enhanced the necrosis following 1- and 4-pulse irradiation.

Further validation of these results was obtained using flow cytometry analysis (SSC-Side Scattering; FL3-488 nm excitation channel) of the entire irradiated suspensions (10,000 cells) 15 hours post irradiation. FIGS. 13A-H show fluorescence activated cell sorting analysis of lymphoma B cells following no irradiation (FIGS. 13A and 13B) and irradiation by 1 pulse (FIGS. 13C and 13D), 4 pulses (FIGS. 13E and 13F) and 16 pulses (FIGS. 13G and 13H). FIGS. 13A, 13C, 13E and 13G show cells targeted by anti-CD20 gold nanoparticles, and FIGS. 13B, 13D, 13F and 13H show not targeted cells. The Red data points represent dead cells. The data show approximately 19%, 46% and 50%, necrosis following 1-, 4- and 16-pulse irradiation, respectively.

To verify the specificity of the damage generated by anti-EGFR gold nanospheres to EGFR over-expressing cells, both A431 and BJAB cells were incubated with anti-EGFR gold nanoparticles, washed off the unbound particles, and irradiated by 8 pulses for fusion induction or by 10 pulses for necrosis induction.

FIGS. 14A-D are images demonstrating fusion specificity to EGFR-expressing cells. The Scale bars represent 50 µm. FIGS. 14A and 14B show A431 cells conjugated to anti-EGFR gold nanospheres before (FIG. 14A) and after (FIG. 14B) irradiation by 8 pulses. Margins of multi-nucleated cells are marked by white dashed curves. FIGS. 14C and 14D show BJAB cells incubated with anti-EGFR nanospheres, before (FIG. 14C) and after (FIG. 14C) irradiation by 8 pulses. Red nuclei indicate necrotic cells. As shown, while about 20% of the A431 cells have been fused together 3 hours after irradiation (FIG. 14B), BJAB cells incubated with anti-EGFR nanoparticles did not show any noticeable effect (FIG. 14D).

FIGS. 15A-D are images demonstrating necrosis specificity to EGFR-expressing cells. The Scale bars represent 50 µm. FIGS. 15A and 15B show A431 cells conjugated to anti-EGFR gold nanospheres before (FIG. 15A) and after (FIG. 15B) irradiation by 10 pulses, and FIGS. 15C and 15D show BJAB cells incubated with anti-EGFR nanospheres before (FIG. 15C) and after (FIG. 15D) irradiation by 10 pulses. As shown, A431 cells incubated with anti-EGFR gold nanoparticles and irradiated by 10 pulses exhibited 50% necrosis 30 minutes after irradiation (FIG. 15B), while irradiated BJAB cells which were incubated with the same particles did not show noticeable effect (FIG. 15D).

In order to demonstrate specificity between cells of similar type, BJAB cells and K562 myelogenous leukemia cells, which do not express CD20, were both incubated with anti-CD20 gold nanoparticles and irradiated by 5 pulses after washing off the unbound particles.

FIGS. 16A-F demonstrate specific induction of necrosis in B-cells. FIGS. 16A and 16B show BJAB cells conjugated to anti-CD20 gold nanospheres before (FIG. 16A) and after (FIG. 16B) irradiation by 5 pulses. FIG. 16C is a flow cytometry analysis plot of the irradiated BJAB cells with (red curve) and without (blue curve) anti-CD20 gold nanoparticles FIG. 16D show K562 cells incubated with anti-CD20 gold nanospheres before (FIG. 16D) and after (FIG. 16E) irradiation by 5 pulses. FIG. 16F shows a flow cytometry analysis plot of the irradiated K562 cells with (red curve) and without (blue curve) anti-CD20 gold nanoparticles. Scale bars represent 50 µm, and red nuclei indicate necrotic cells.

The phase and fluorescence microscopy images of the cell lines have shown considerable necrosis of BJAB cells (FIG. 16B) and no apparent necrosis of the K562 cells which do not express CD20. Flow cytometry analysis of the cells' viability has confirmed the difference in necrosis rates, showing 38% BJAB necrosis 17 hours following irradiation (FIG. 16C) and only 3.2% necrosis in the K562 cells (FIG. 16F).

Tuning the energy delivered by each individual pulse provides another mean for selecting the type of manipulation. In order to study the effect of pulse energy, fusion and necrosis rates of irradiated BJAB cells were quantified for different pulse fluence levels, while the number of irradiating pulses was kept constant (16 pulses) for all experiments. Below 10 mJ/cm$^2$ per pulse in a series of 16 pulses, no multi-nucleated cells were observed and a negligible increase (less than 3%) in necrosis rate was evident (FIG. 11C). At 25 mJ/cm$^2$ per pulse, the fusion rate reached a peak value of 35% of the cells, 30% higher than the fusion rate obtained at 35 mJ/cm$^2$ per pulse. Pulse fluence above 35 mJ/cm$^2$ caused widespread cell death (mainly necrosis) throughout the sample, similarly to the results obtained with the epidermoid carcinoma cells (FIG. 9A).

The present inventors found that cell fusion and necrosis could be induced also by adding non-specific (no targeting molecule) gold nanoparticles to the cells' growth medium, and irradiating the cells using pulse parameters (wavelength, fluence, pulse number) that are similar to those used with antibody-conjugated particles.

FIGS. 12A1-12A6 and 12B1-12B6 show time sequence fluorescence images obtained during experiments with non-specific gold nanoparticles. FIGS. 12A1-12A6 show shows time sequence of fluorescence images of fusing BJAB cells superimposed on phase contrast images, following irradiation by 5 pulses of 35 mJ/cm$^2$ in the presence of non-specific gold nanoparticles. The plasma membranes were green labeled. the formation of a hybridoma cell is shown in FIGS. 12B1-12B6, which include a time sequence of fluorescence images of human BJAB cells (red nuclei) and murine (NSO) cells (blue nuclei) superimposed on phase contrast images, following irradiation of 5 pulses of 35 mJ/cm$^2$ in the presence of non-specific gold nanoparticles. The scale bars represent 10 µm.

FIGS. 12A1-12A6 reveal the gradual formation of a multi-nucleated cell from four identical BJAB cells whose nuclei were labeled with different blue and red fluorescent dyes. The fusion process, as captured in a sequence of fluorescence images superimposed on phase contrast images, was nearly completed three minutes after irradiation, as evident by the apparent uniform plasma membrane (green) surrounding the four nuclei. Multinucleated cells comprising of up to 20 nuclei were observed in several experiments, depending on the mutual proximity of the individual cells prior to irradiation.

In order to demonstrate the potential of the technique of the present embodiments to form hybridoma cells, a mixture of B cells of human origin (BJAB cells, red stained nuclei) and cells of murine origin (myeloma NSO cells, blue stained nuclei) were incubated in a medium containing non-specific nanoparticles and irradiated by 5 pulses (35 mJ/cm$^2$ per pulse) at resonance (550 nm) wavelength. FIGS. 12B1-12B6 show that nuclei of both cells were completely engulfed by a uniform, single membrane less than eight minutes past irradiation. In this experiment, fusion rate was about 3-6%. Higher fusion rates can be achieved according to some embodiments of the present invention by repeating the irradiation sequence multiple times, or by optimizing the biological and physical parameters of the experiments.

The present examples demonstrate that interaction between intense laser pulses and gold nanoparticles can be used to manipulate cells. When gold nanoparticles are irradiated by pulses that are much shorter than their typical heat diffusion time constants, the pulse energy is released into the medium in the form of a shockwave which is known to extend up to a few tens of nanometers from the particle's surface. Improving the physical specificity (typically by maintaining high localization) of the effect is achieved by tuning the pulses' wavelength to the plasmonic resonance of the gold nanoparticles and by specifically targeting the nanoparticles to a desired cell population or to specific intracellular organelles.

The interaction between the nanometric shockwave and the cells depends on several physical and biological parameters, which can be selected according to some embodiments of the present invention to effect the desired manipulation.

The present examples demonstrate manipulations of cell-lines which represent two different types of malignancies: one of epithelial origin and the other of lymphoid origin. The low toxicity and high spatial selectivity of the present embodiments allows to target cell populations while maintaining low collateral damage to healthy cells, for example by increasing nanoparticle concentration or by repeating the irradiation procedure multiple times. Specific induction of apoptosis is beneficial for clinical applications that are sensitive to inflammation which could occur due to uncontrolled spillage of cellular content.

For malignant tumors which exhibit high level of resistance to apoptosis, the induction of necrosis is preferred over apoptosis. An example for such an application is the use of necrotic tumor cell lysates for the production of cancer vaccines, which are used to stimulate the immune system of chronic B lymphocytic leukemia patients to detect and attack 'self' cancerous B cells. The potential use of Rituximab, an FDA approved anti-CD20 monoclonal antibody drug for the treatment of B-cell leukemia and non-Hodgkin lymphomas, for targeting gold nanoparticles to B cells is particularly advantageous for such an application, as the antibody molecules further enhances and complements the effect of the laser pulses.

Specific induction of cell fusion is useful for numerous applications in drug development and cancer research. Conventional methods for cell fusion often involve the addition of PEG to the cell medium, application of high voltage across the cells' plasma membranes, and the use of viruses. Specific fusion is useful, for example, for generating hybridoma cells for the production of monoclonal antibodies, and for the generation of autologous cancer vaccination by fusing cancer cells with dendritic cells. Using nanoparticles with specific targeting antibodies allows the technique of the present embodiments to affect only selected cells, and avoid significant collateral damage to nearby cells and tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of fusing at least two cells, comprising, directing a pulsed optical field to at least one conductive nanoparticle contacting the at least two cells, so as to generate in said cells a pressure wave selected to effect cell-fusion, wherein said pulsed optical field is a laser characterized by pulse duration of from about 6 fs to about 10 ns; wherein said directing said pulsed optical field to said nanoparticle comprises selecting the number of pulses of said optical field so as to induce said cell-fusion.

2. The method according to claim 1, wherein said directing said pulsed optical field comprises directing said pulsed optical field to a conductive nanoparticle that is attached to at least one of the cells.

3. The method according to claim 1, wherein said directing said pulsed optical field comprises directing said pulsed optical field to a conductive nanoparticle that is attached to the at least two cells.

4. The method according to claim 1, wherein said directing said pulsed optical field comprises directing said pulsed optical field to a nanoparticle that comprises an affinity component having affinity to at least one of the cells.

5. The method according to claim 1, comprising effecting thermal expansion of said nanoparticle by said pulsed optical field.

6. The method according to claim 1, wherein said directing said pulsed optical field comprises directing said pulsed optical field to a nanoparticle that is a nanosphere.

7. The method according to claim 1, wherein said directing said pulsed optical field comprises directing a pulsed optical field that is characterized by a pulse duration from about 6 fs to about 200 fs.

8. The method according to claim 1, wherein said pulsed optical field is characterized by a pulse duration in a picoseconds time scale.

9. The method according to claim 1, wherein said directing said pulsed optical field comprises directing a pulsed optical field having a wavelength of from about 520 nm to about 580 nm.

10. The method according to claim 1, wherein said directing said pulsed optical field comprises directing a pulsed optical field having a wavelength of about 550 nm.

11. The method according to claim 1, wherein said directing said pulsed optical field comprises directing a pulsed optical field that is characterized by a pulsed rate of less than 10 kHz.

12. The method according to claim 1, wherein said directing said pulsed optical field comprises directing a pulsed optical field that is characterized by a pulsed rate of about 1 kHz.

13. The method according to claim 1, wherein said directing said pulsed optical field to said nanoparticle is done ex-vivo.

14. The method according to claim 1, wherein said at least two cells are identical.

15. The method according to claim 1, wherein said directing said pulsed optical field comprises selecting the number of pulses of said optical field so as to induce cell-fusion between two non-identical cells.

16. The method according to claim 15, wherein said non-identical cells comprise tumor cells and dendritic cells.

17. The method according to claim 15, wherein said non-identical cells comprise stem cells and somatic cells.

18. The method according to claim 17, wherein said stem cells are embryonic stem cells.

19. The method according to claim 17, wherein said somatic cells are muscle cells or bone cells.

20. The method according to claim 1, wherein said directing said pulsed optical field comprises selecting the number of pulses of said optical field so as to induce cell-fusion between two primary cells.

21. The method according to claim 1, wherein said cells comprise immortalized cells.

22. The method according to claim 1, wherein said directing said pulsed optical field comprises selecting the number of pulses of said optical field so as to induce cell-fusion between tumor cells and antibody producing cells.

23. The method according to claim 1, wherein said directing said pulsed optical field comprises selecting the number of pulses of said optical field so as to induce cell-fusion between tumor cells and antibody producing cells that are B lymphocytes.

24. The method according to claim 23, wherein said B lymphocytes are peripheral blood mononuclear cells.

25. The method according to claim 23, wherein said B lymphocytes are murine splenic B cells.

26. The method according to claim 1, wherein said directing said pulsed optical field comprises selecting the number of pulses of said optical field so as to induce cell-fusion between tumor cells and antibody producing cells that are human B lymphocytes.

27. The method according to claim 1, wherein at least one of the cells is a part of a pathological tissue.

28. The method according to claim 1, wherein said directing said pulsed optical field to said nanoparticle comprises inserting a light transmitting device into the body of a living subject having the at least two cells therein.

29. The method according to claim 28, wherein said inserting said light transmitting device into the body is by endoscopy.

30. The method according to claim 28, wherein said inserting said light transmitting device into the body is by laparoscopy.

31. The method according to claim 1, comprising inducing said cavitations without ionizing said at least two cells.

32. The method according to claim 1, wherein said at least one conductive nanoparticle comprises a solid surface conjugated with at least two affinity components having affinity to two or more different types of cells.

33. A method of generating a monoclonal antibody, comprising:

directing a pulsed laser characterized by a pulse rate of 10 kHz or less, and pulse duration of from about 10 fs to about 10 ns, to at least one conductive nanoparticle contacting an immortalizing cell and an antibody producing cell, so as to generate in said cells a pressure wave selected to effect fusion between said immortalizing cell and said antibody producing cell, thereby obtaining a hybridoma; and cloning said hybridoma;

wherein said directing said pulsed optical field to said nanoparticle comprises selecting the number of pulses of said optical field so as to induce said cell-fusion.

34. The method of claim 33, further comprising harvesting the monoclonal antibody following said cloning.

* * * * *